(12) United States Patent
Petry et al.

(10) Patent No.: US 7,208,504 B2
(45) Date of Patent: Apr. 24, 2007

(54) BICYCLIC INHIBITORS OF HORMONE SENSITIVE LIPASE

(75) Inventors: Stefan Petry, Frankfurt (DE); Karl-Heinz Baringhaus, Wölfersheim (DE); Norbert Tennagels, Frankfurt (DE); Guenter Mueller, Sulzbach (DE); Hubert Heuer, Schwabenheim (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 559 days.

(21) Appl. No.: 10/685,199

(22) Filed: Oct. 14, 2003

(65) Prior Publication Data
US 2004/0127484 A1 Jul. 1, 2004

Related U.S. Application Data

(60) Provisional application No. 60/446,913, filed on Feb. 12, 2003.

(30) Foreign Application Priority Data
Oct. 12, 2002 (DE) .................. 102 47 680

(51) Int. Cl.
*A61K 31/445* (2006.01)
*A61K 31/4192* (2006.01)
*C07D 211/14* (2006.01)
*C07D 249/18* (2006.01)

(52) U.S. Cl. ............... 514/322; 514/322; 514/359; 546/210; 548/257

(58) Field of Classification Search ......... 546/210; 548/257; 514/322, 359
See application file for complete search history.

(56) References Cited

U.S. PATENT DOCUMENTS

| 4,255,510 A * | 3/1981 | Simons et al. ............ 430/219 |
| 4,256,881 A * | 3/1981 | Simons et al. ............ 544/132 |
| 6,221,633 B1 | 4/2001 | Ertl et al. |
| 6,221,897 B1 | 4/2001 | Baringhaus et al. |
| 6,245,744 B1 | 6/2001 | Baringhaus et al. |
| 6,342,512 B1 | 1/2002 | Kirsch et al. |

FOREIGN PATENT DOCUMENTS

| EP | 0 462 884 A1 | 12/1991 |
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 99/15525 | 4/1999 |
| WO | WO 00/40569 | 7/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 A1 | 11/2000 |
| WO | WO 01/09111 A1 | 2/2001 |
| WO | WO 01/17981 | 3/2001 |
| WO | WO 01/83451 A1 | 11/2001 |
| WO | WO 01/85695 A1 | 11/2001 |
| WO | WO 02/090355 A1 | 11/2002 |
| WO | WO 03/020269 | 3/2003 |
| WO | WO 03/051842 A2 | 6/2003 |

OTHER PUBLICATIONS

Katritsky, Alan R. et al, "The Direct Carbamoylation of Organometallic Reagents with 1,2,3-Benzotriazole-1-carboxamides," J. Chem. Research(S),1999, pp. 230-231.*
Simons, Michael J. et al, "Development restrainer precursors for photograhoic elements," Research Disclosure Journal No. 19126, (1980). pp. 1-8.*
Asakawa A et al., Cocaine-Amphetamine-Regulated Transcript Influences Energy Metabolism, Anxiety and Gastric Emptying in Mice, Hormone and Metabolic Research, 2001, 33(9), pp. 554-558.
Fredrikson G et al, Hormone-sensitive Lipase of Rat Adipose Tissue, J. Biol. Chem., 1981, vol. 256, No. 12, pp. 6311-6320.
Katritzky Alan R et al., A General Synthesis of Unsymmetrical Tetrasubstituted Ureas, Journal of Organic Chemistry, 1997, 62(12), 4155-4158.
Katritzky Alan R et al., The Direct Carbamoylation of Oranometallic Reagents with 12,3-Benzotriazole-1-carboxamides, J. Chem. Research (S), 1999, pp. 230-231.
Lee Daniel W et al., Leptin agonists as a potential approach to the treatment of obesity, Drugs of the Future, 2001, 26(9), pp. 873-881.
Nilsson S et al., Purification of Hormone-Sensitive Lipase by High-Performance Ion Exchange Chromatography, Anal. Biochem., 1986, vol. 158, pp. 399-407.
Okada Hiroshi et al., Synthesis and Antitumor Activities of Prodrugs of Benzoylphenylureas, Chem. Pharm. Bull. 1994, vol. 42(1), pp. 57-61.

(Continued)

*Primary Examiner*—Kamal A. Saeed
*Assistant Examiner*—Janet L Coppins
(74) *Attorney, Agent, or Firm*—Irving Newman

(57) ABSTRACT

Benzotriazoles of formula I

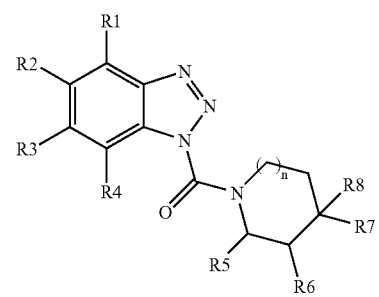

in which R1 to R8 have the abovementioned meanings and process for their preparation are described. The compounds show an inhibitory effect on hormone-sensitive lipase.

13 Claims, No Drawings

OTHER PUBLICATIONS

Patkar S et al., Lipase inhibitors, Lipases their structure, biochemistry and application, Cambridge University Press, pp. 207-224.

Salvador Javier et al., Perspectives in the therapeutic use of leptin, Expert Opinion on Pharmacotherapy 2001, 2(10), 1615-1622.

Tornqvist H et al., Purification and Some Properties of a Monoacylglycerol-hydrolyzing Enzyme of Rat Adipose Tissue, J. Biol. Chem., 1976, vol. 251, No. 3, pp. 813-819.

Winzell Maria Sorhede et al., Pancreatic Beta-Cell Lipotoxicity Induced by Overexpression of Hormone-Sensitive Lipase, Diabetes, 2003, vol. 52, pp. 2057-2065.

Zunft H J F et al., Carob Pulp Preparation for Treatment of Hypercholesterolemia, Advances in Therapy, 2001, 18(5), pp. 230-236.

* cited by examiner

BICYCLIC INHIBITORS OF HORMONE SENSITIVE LIPASE

CROSS-REFERENCE TO RELATED APPLICATIONS

This application claims the benefit of priority of German Patent Application No. 10247680.2-44, filed Oct. 12, 2002, as well as the benefit of U.S. Provisional Patent Application No. 60/446,913, filed Feb. 12, 2002.

FIELD OF THE INVENTION

Benzotriazoles of formula I

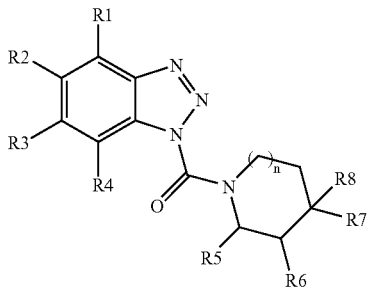

in which R1 to R8 have the meanings set forth below, and process for their preparation are described. The compounds show an inhibitory effect on hormone-sensitive lipase.

BACKGROUND OF THE INVENTION

Benzotriazoles are already known from a wide range of fields, such as for example photochemistry (U.S. Pat. No. 4,255,510, Kodak) or as orexin antagonists (WO 02/090355, SKB). Also, the synthesis for preparing benzotriazoles has been described by Katritzky et al. in J. Org. Chem. 1997, 62, 4155–4158. Also known are carbamates for use as lipase inhibitors such as, for example, Shamkant Patkar et al. in Paul Woolley, Steffen B. Petterson (ed), Lipase (1994) 207–227 or WO 03/051842.

SUMMARY OF THE INVENTION

Surprisingly, it has now been possible to show that the benzotriazoles of the present invention show activity with regard to HSL, hormone sensitive lipase.

The invention relates to benzotriazoles of formula I,

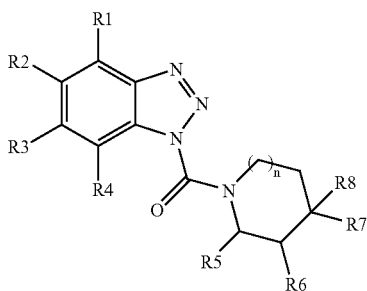

in which:
n is an integer selected from 0, 1 and 2
R1 to R8 are each H, except that one of R2 and R3 may be selected from
Br, Cl, $CH_3$, CN, $NH_2$, $NO_2$, $CF_3$, $OCH_3$, phenoxy, benzoyl, CH(OH)-phenyl, S-cyclohexyl, and CO—$OCH_3$; or
R1 is Cl and R3 is $CF_3$; or
R2 is F and R3 is Cl; or
on of R6 and R7 may be selected as follows:
R6 is $CH_3$ or R7 is selected from $CH_3$, $C_2H_5$, $CH(CH_3)_2$, $C(CH_3)_3$, $CF_3$, Br, Cl, benzyl and CO—$OC_2H_5$; or
R6 and R7 each are $CH_3$; or
R6 and R7 may be replaced by a double bond between the ring carbons to which they are attached; or
R6 and R7 may, in combination with the carbon to which they are attached, form a benzo-fused ring or, when n is 0, may form cyclohexanediyl, the ring formed from R6, R7 and the carbons to which they are attached being optionally substituted singly by $NH_2$ or $NO_2$ or substituted singly or doubly by $OCH_3$; and
R7 and R8, together with the carbon to which they are attached, may form cyclopentyl, diazirine or =$CH_2$; provided, however, that when R1 to R5 and R8 are H, and R6, R7 and the carbons to which they are attached form a benzo-fused ring, n is not 1, and when R1 and R3–R8 are H and R2 is $CH_3$, n is not 1.

The invention relates to compounds of formula I in the form of their racemates, racemic mixtures and pure enantiomers and to their diastereomers and mixtures thereof. The alkyl radicals may be either straight-chain or branched. Halogen may be fluorine, chlorine or bromine, in particular fluorine or chlorine.

DETAILED DESCRIPTION OF THE INVENTION

Preference is given to benzotriazoles of formula I in which:
R1 to R8 are each H, except that one of R2 and R3 may instead be selected from the following substituents:
R2 is selected from Br, Cl, CN, $NO_2$, $CF_3$, $OCH_3$, phenoxy, benzoyl, CH(OH)-phenyl, S-cyclohexyl, and CO—$OCH_3$; or
R3 is selected from $CH_3$, CN, Br, Cl, $NH_2$, $NO_2$, and benzoyl.

Particular preference is given to the benzotriazoles of formula I in which:
R1 to R8 are each H; except that one of R2 and R3 may instead be selected from the following substituents:
R2 is selected from Br, Cl, $NO_2$, $OCH_3$, phenoxy, and CO—$OCH_3$; or R3 is NH2; or
R2 is F and R3 is Cl; or
n is 1 or 2 and
one of R6 and R7 is selected from the following substituents:
R6 is $CH_3$; or R7 is selected from $CH_3$, $CF_3$ and Br; or
R6 and R7 may be replaced by a double bond between the ring carbons to which they are attached; or
R6 and R7 may, in combination with the carbons to which they are attached, form a benzo-fused ring, which may be optionally substituted singly by $NH_2$ or substituted singly or doubly by $OCH_3$; and
R7 and R8, together with the carbon to which they are attached, form a cyclopentyl; or
n is 0 and
R6 and R7, together with the carbons to which they are attached, form a benzo-fused ring or cyclohexanediyl; as well as to benzotriazoles of formula I in which R1 to R8 are each H; except that one of R2 and R3 may instead be selected from the following substituents:

R2 is selected from Br, CN, CF$_3$, OCH$_3$, phenoxy, benzoyl, CH(OH)-phenyl, and S-cyclohexyl; or R3 is selected from CN, Br, Cl, NO$_2$, and benzoyl; or R1 is Cl and R3 is CF$_3$; or n is 1 and one of R6 and R7 is selected from the following substituents:

R6 is CH$_3$; or

R7 is selected from CH$_3$, C$_2$H$_5$; CH(CH$_3$)$_2$, C(CH$_3$)$_3$, benzyl and CO—OC$_2$H$_5$; or R6 and R7 are each CH$_3$; or R6 and R7 may be replaced by a double bond between the ring carbons to which they are attached; or R5 and R6 or R6 and R7 may, in combination with the carbons to which they are attached, form a benzo-fused ring;

provided, however, that when R1 to R5 and R8 are H and R6, R7 and the carbon to which they are attached form a benzo-fused ring, n is not 1.

Very particular preference is given to the benzotriazoles having the following structures:

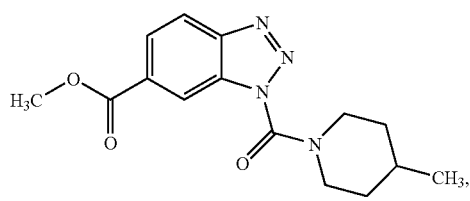

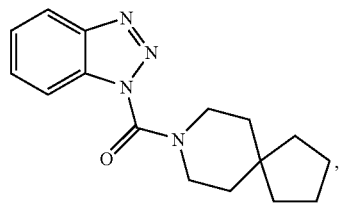

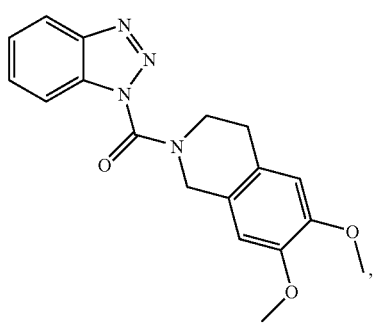

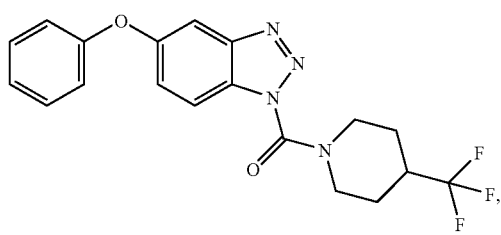

-continued

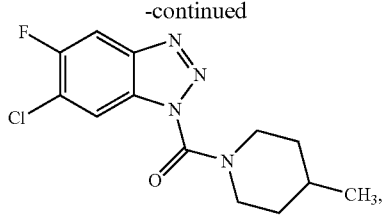

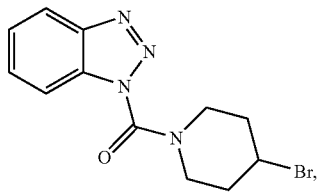

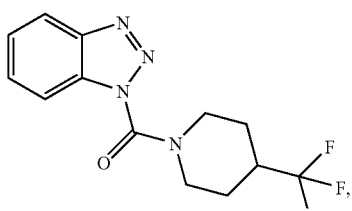

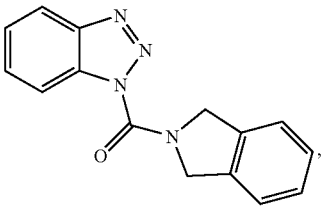

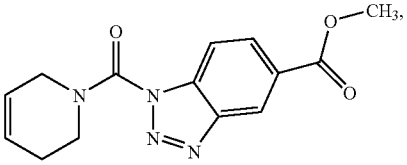

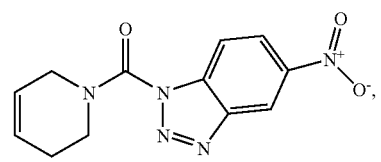

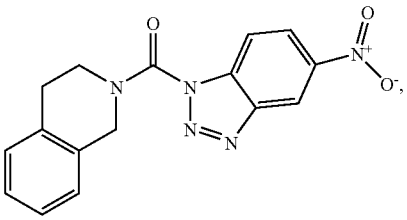

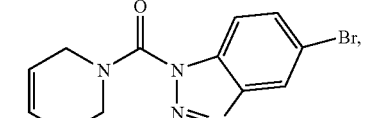

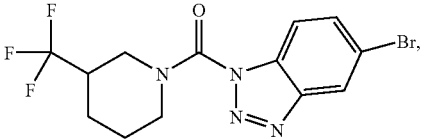

-continued
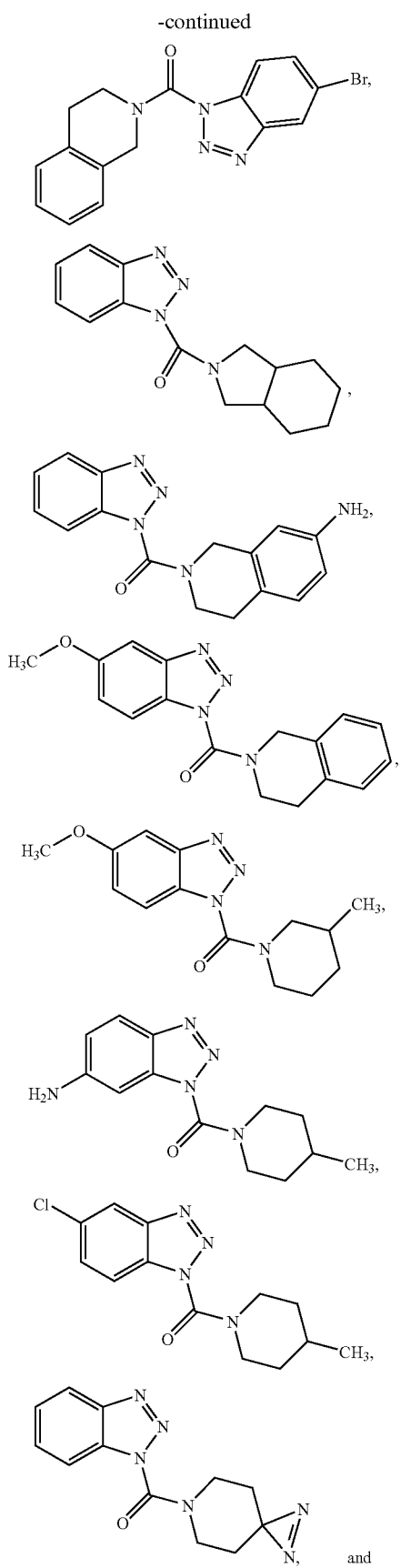
and
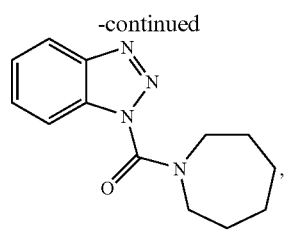
as well as the benzotriazoles having the following structures:
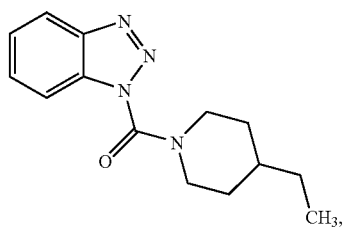
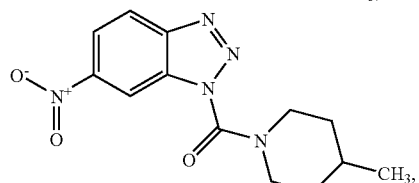
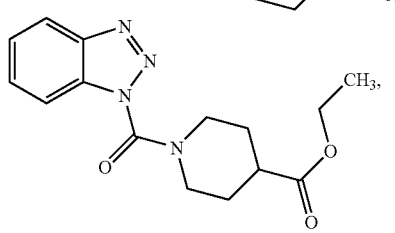
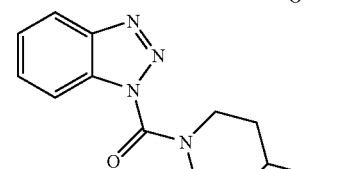
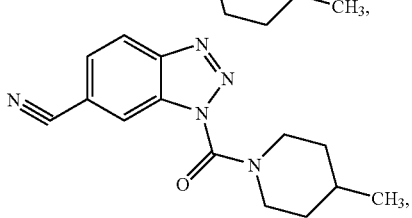
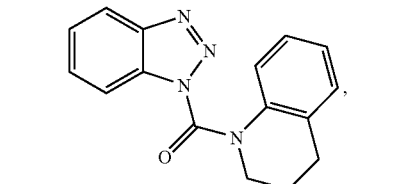
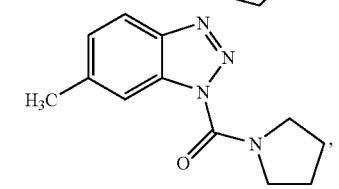

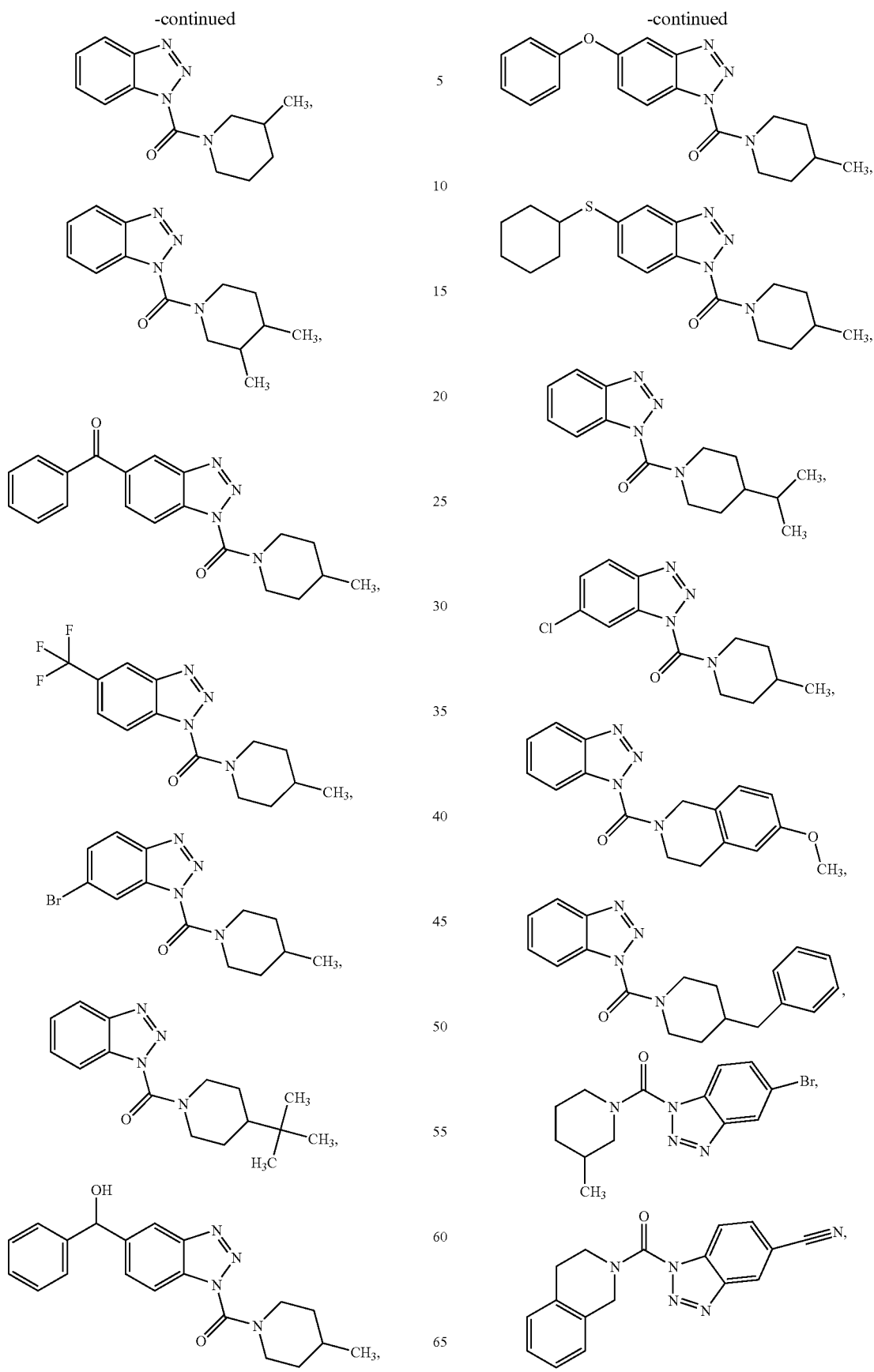

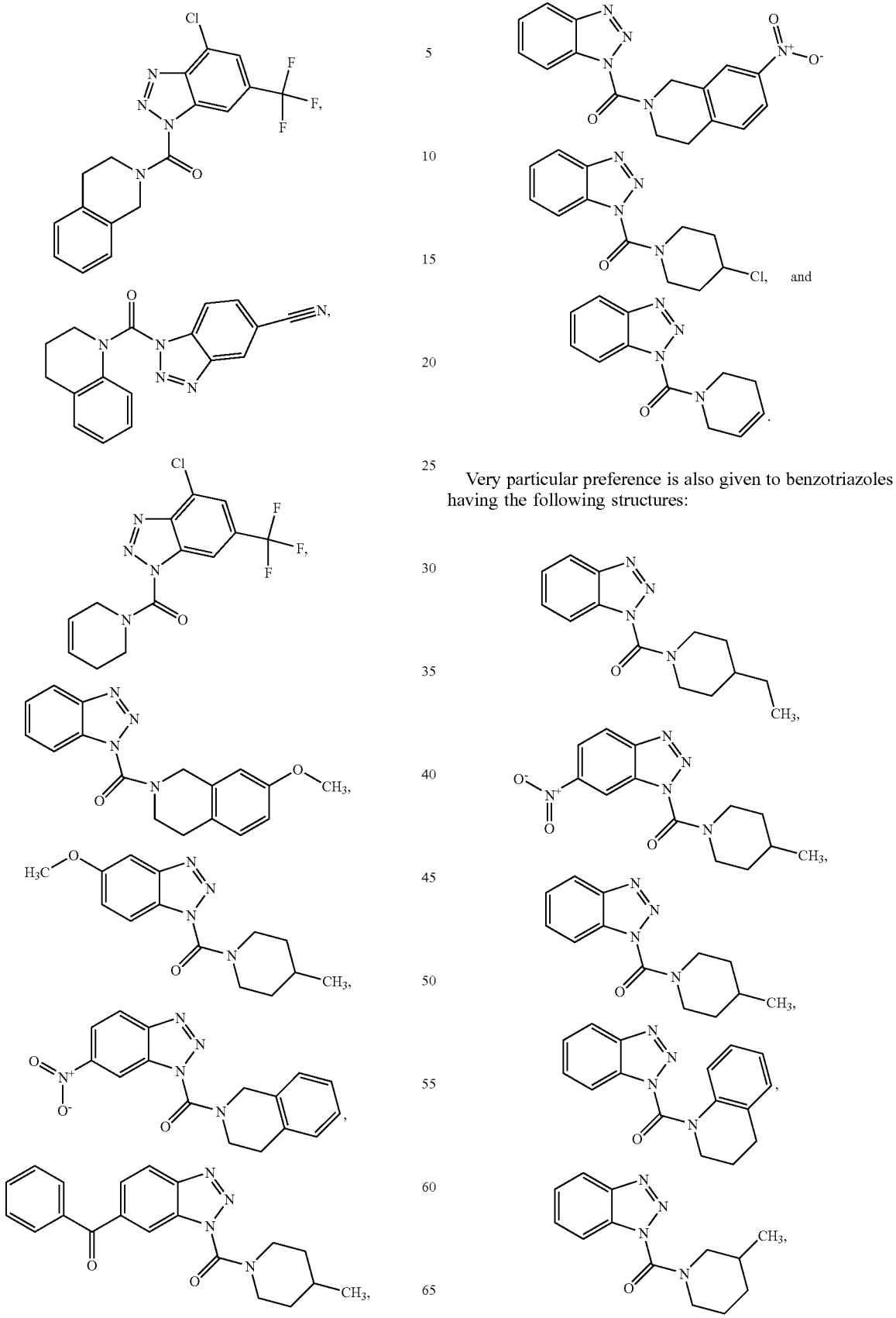
Very particular preference is also given to benzotriazoles having the following structures:

-continued

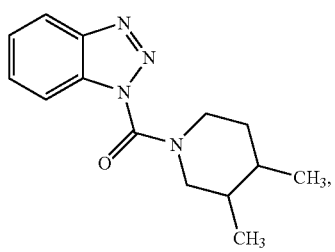
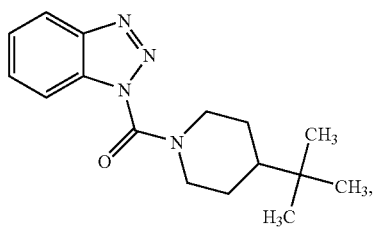
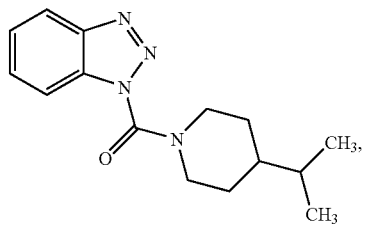
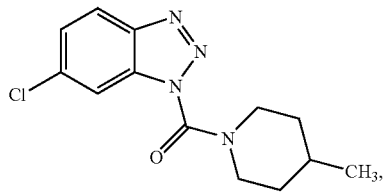
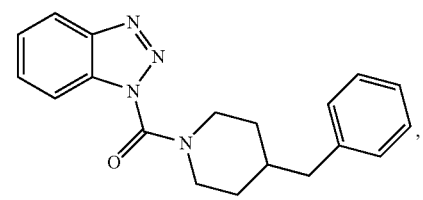
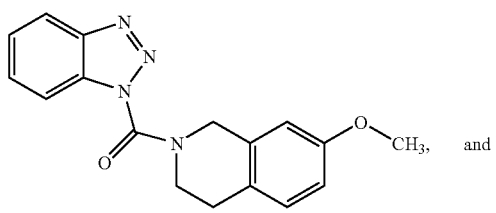
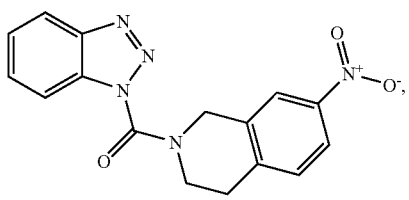

as well as the benzotriazoles having the following structures:

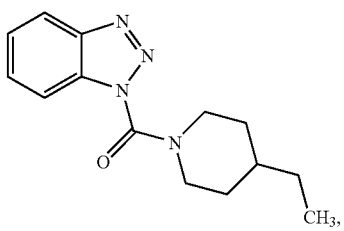
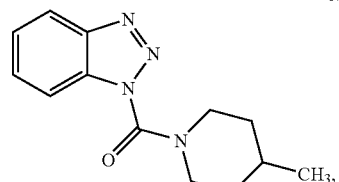
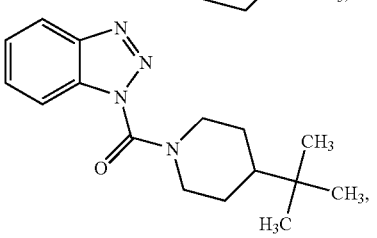
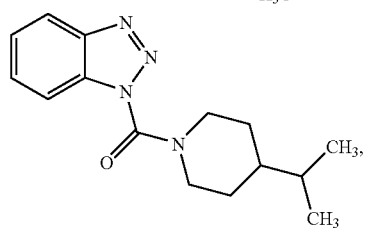
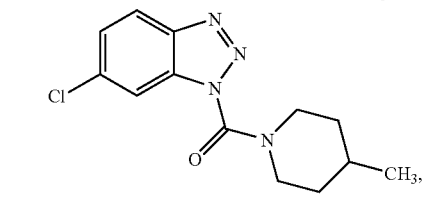
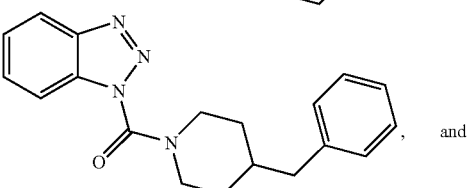, and
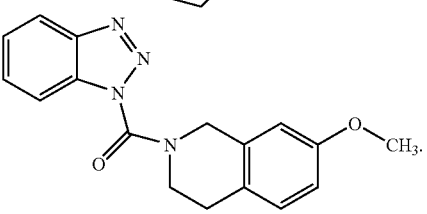

Pharmaceutically acceptable salts are, because their solubility in water is greater than that of the parent or basic compounds, particularly suitable for medical applications. These salts must have a pharmaceutically acceptable anion or cation. Suitable pharmaceutically acceptable acid addition salts of the compounds of the invention are salts of inorganic acids, such as, hydrochloric acid, hydrobromic, phosphoric, metaphosphoric, nitric and sulfuric acid, as well as salts of organic acids, such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine and ethylenediamine.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of formula I of the invention, for example an ester, which, on administration to a mammal such as, for example, a human is able to form (directly or indirectly) a compound of formula I or an active metabolite thereof. Physiologically functional derivatives also include prodrugs of the compounds of the invention, as described, for example, in H. Okada et al., Chem. Pharm. Bull. 1994, 42, 57–61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of formula I as described above, and their salts, solvates and physiologically functional derivatives as described herein.

The compound(s) of formula (I) may also be administered in combination with other active ingredients.

The amount of a compound of formula I necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg and 50 mg) per day per kilogram of body weight, for example, 3–10 mg/kg/day. An intravenous dose may be, for example, in the range from 0.3 mg to 1.0 mg/kg, which can suitably be administered as infusion of 10 ng to 100 ng per kilogram per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations, which can be administered orally, such as, for example, capsules or tablets, may contain, for example, from 1.0 to 1000 mg, typically from 10 to 600 mg. For the therapy of the above-mentioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both, and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention include those suitable for oral, rectal, topical, per oral (for example, sublingual) and parenteral (for example, subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings that are resistant to gastric juice comprise cellulose acetate phthalate, polyvinyl acetate phthalate, hydroxypropylmethylcellulose phthalate and anionic polymers of methacrylic acid and methyl methacrylate. Suitable pharmaceutical compositions for oral administration may be in the form of separate units such as, for example, capsules, wafers, tablets or lozenges (suckable tablets), each of which contain a defined amount of a compound of formula I; as powders or granules, as solutions or suspensions in an aqueous or nonaqueous liquid; or as oil-in-water or water-in-oil emulsions. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (more) surface-active/dispersing agent in a suitable machine. Molded tablets can be produced by molding the compound, which is in powder form and is moistened with an inert liquid diluent, in a suitable machine.

Pharmaceutical compositions which are suitable for per-oral (sublingual) administration comprise lozenges (suckable tablets) which contain a compound of formula I with a flavoring agent, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of formula I with one or more conventional solid carriers, for example, cocoa butter, and shaping the resulting mixture.

Pharmaceutical compositions suitable for topical use on the skin are preferably in the form of ointment, cream, lotion, paste, spray, aerosol or oil. Carriers which can be used include petrolatum, lanolin, polyethylene glycols, alcohols and combinations of two or more of these substances. The active ingredient is generally present in a concentration of from 0.1 to 15% by weight of the composition, for example, from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution, which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

Further Active Ingredients Suitable for Combination Products Are:

all antidiabetics mentioned in the Rote Liste 2001, chapter 12. They may be combined with the compounds of formula I of the invention, in particular, for a synergistic improvement of the effect. Administration of the active ingredient combination may take place either by separate administration of the active ingredients to the patient or in the form of combination products in which a plurality of active ingredients are present in one pharmaceutical preparation. Most of the active ingredients listed below are disclosed in the USP Dictionary of USAN and International Drug Names, US Pharmacopeia, Rockville 2001. Suitable antidiabetics include insulin and insulin derivatives such as, for example, Lantus® (see www.lantus.com), fast-acting insulins (see U.S. Pat. No. 6,221,633), GLP-1 derivatives such as, for example, those disclosed in WO 98/08871 of Novo Nordisk A/S, and orally effective hypoglycemic active ingredients.

The orally effective hypoglycemic active ingredients include sulfonylureas, biguanidines, meglitinides, oxadiazolidinediones, thiazolidinediones, glucosidase inhibitors, glucagon antagonists, GLP-1 agonists, potassium channel openers such as, for example, those disclosed in WO 97/26265 and WO 99/03861 of Novo Nordisk A/S, insulin sensitizers, inhibitors of liver enzymes involved in the stimulation of gluconeogenesis and/or glycogenolysis, modulators of glucose uptake, compounds which alter lipid metabolism, such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of formula I are administered in combination with an HMG-CoA reductase inhibitor, such as simvastatin, fluvastatin, pravastatin, lovastatin, atorvastatin, cerivastatin, or rosuvastatin.

In one embodiment of the invention, the compounds of formula I are administered in combination with a cholesterol absorption inhibitor, such as, for example, ezetimibe, tiqueside, or pamaqueside.

In one embodiment of the invention, the compounds of formula I are administered in combination with a PPAR gamma agonist, such as, for example, rosiglitazone, pioglitazone, JTT-501, or GI 262570.

In one embodiment of the invention, the compounds of formula I are administered in combination with a PPAR alpha agonist, such as, for example, GW 9578, or GW 7647.

In one embodiment of the invention, the compounds of formula I are administered in combination with a mixed PPAR alpha/gamma agonist, such as, for example, GW 1536, or as described in WO 00/64888, WO 00/64876, or WO 03/020269.

In one embodiment of the invention, the compounds of formula I are administered in combination with a fibrate, such as, for example, fenofibrate, clofibrate, or bezafibrate.

In one embodiment of the invention, the compounds of formula I are administered in combination with an MTP inhibitor, such as, for example, implitapide, BMS-201038, or R-103757.

In one embodiment of the invention, the compounds of formula I are administered in combination with a bile acid absorption inhibitor (see, for example, U.S. Pat. No. 6,245, 744 or U.S. Pat. No. 6,221,897).

In one embodiment of the invention, the compounds of formula I are administered in combination with a CETP inhibitor, such as, for example, JTT-705.

In one embodiment of the invention, the compounds of formula I are administered in combination with a polymeric bile acid adsorbent, such as, for example, cholestyramine, or colesevelam.

In one embodiment of the invention, the compounds of formula I are administered in combination with an LDL receptor inducer (see U.S. Pat. No. 6,342,512).

In one embodiment of the invention, the compounds of formula I are administered in combination with an ACAT inhibitor, such as, for example, avasimibe.

In one embodiment of the invention, the compounds of formula I are administered in combination with an antioxidant, such as, for example, OPC-14117.

In one embodiment of the invention, the compounds of formula I are administered in combination with a lipoprotein lipase inhibitor, such as, for example, NO-1886.

In one embodiment of the invention, the compounds of formula I are administered in combination with an ATP-citrate lyase inhibitor, such as, for example, SB-204990.

In one embodiment of the invention, the compounds of formula I are administered in combination with a squalene synthetase inhibitor, such as, for example, BMS-188494.

In one embodiment of the invention, the compounds of formula I are administered in combination with a lipoprotein (a) antagonist, such as, for example, CI-1027 or nicotinic acid.

In one embodiment of the invention, the compounds of formula I are administered in combination with a lipase inhibitor, such as, for example, orlistat.

In one embodiment of the invention, the compounds of formula I are administered in combination with insulin.

In one embodiment, the compounds of formula I are administered in combination with a sulfonylurea such as, for example, tolbutamide, glibenclamide, glipicide or glimepiride.

In one embodiment, the compounds of formula I are administered in combination with a biguanide, such as, for example, metformin.

In one further embodiment, the compounds of formula I are administered in combination with a meglitinide, such as, for example, repaglinide.

In one embodiment, the compounds of formula I are administered in combination with a thiazolidinedione, such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of formula I are administered in combination with an α-glucosidase inhibitor, such as, for example, miglitol or acarbose.

In one embodiment, the compounds of formula I are administered in combination with an active ingredient which acts on the ATP-dependent potassium channel of the beta cells, such as, for example, tolbutamide, glibenclamide, glipicide, glimepiride or repaglinide.

In one embodiment, the compounds of formula I are administered in combination with more than one of the aforementioned compounds, e.g. in combination with a sulfonylurea and metformin, with a sulfonylurea and acarbose, repaglinide and metformin, insulin and a sulfonylurea, insulin and metformin, insulin and troglitazone, insulin and lovastatin, etc.

In a further embodiment, the compounds of formula I are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554–558), NPY antagonists, e.g. naphthalene-1-sulfonic acid {4-[((4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)), serotonin reuptake inhibitors (e.g. dexfenfluramine), mixed sertoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity, Drugs of the Future (2001), 26(9), 873–881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the other active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615–1622.

In one embodiment, the other active ingredient is dexamphatamine or amphetamine.

In one embodiment, the other active ingredient is fenfluramine or dexfenfluramine.

In another embodiment, the other active ingredient is sibutranine.

In one embodiment, the other active ingredient is orlistat.

In one embodiment, the other active ingredient is mazindol or phentermine.

In one embodiment, the compounds of formula I are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September–October), 18(5), 230–6.) Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of formula I and Caromax®. Caromax® can, in this connection, also be administered in the form of food products, such as, for example, in bakery products or muesli bars.

It will be appreciated that every suitable combination of the compounds of the invention with one or more of the aforementioned compounds and optionally one or more other pharmacologically active substances is regarded as falling within the scope of the present invention.

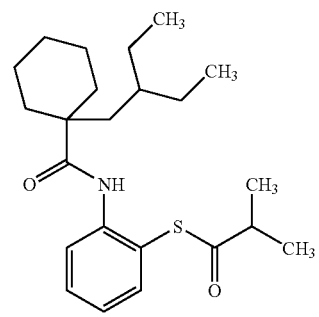

JTT-705

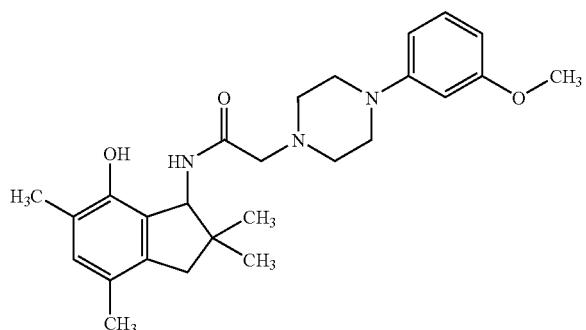

OPC-14117

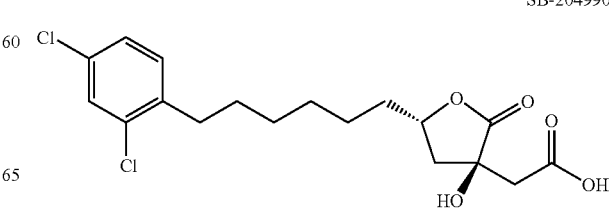

SB-204990

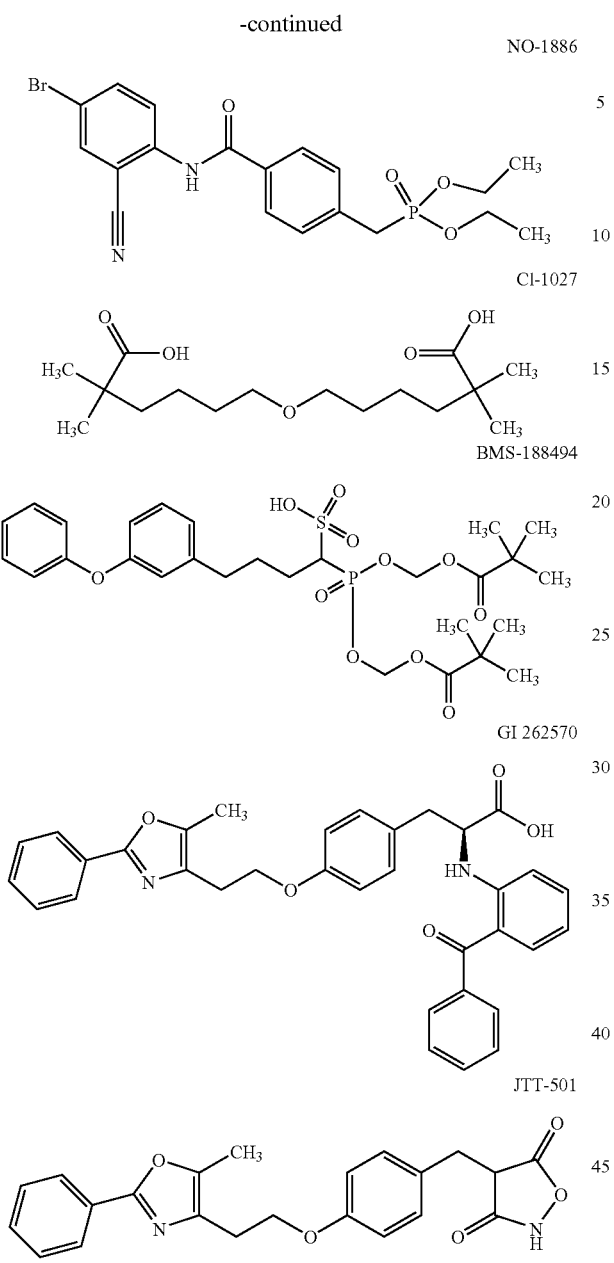

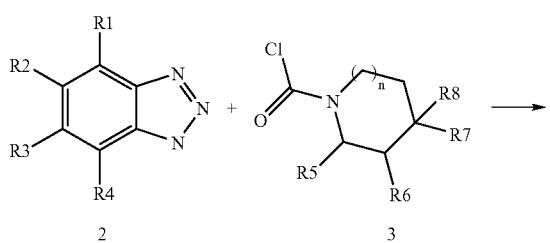

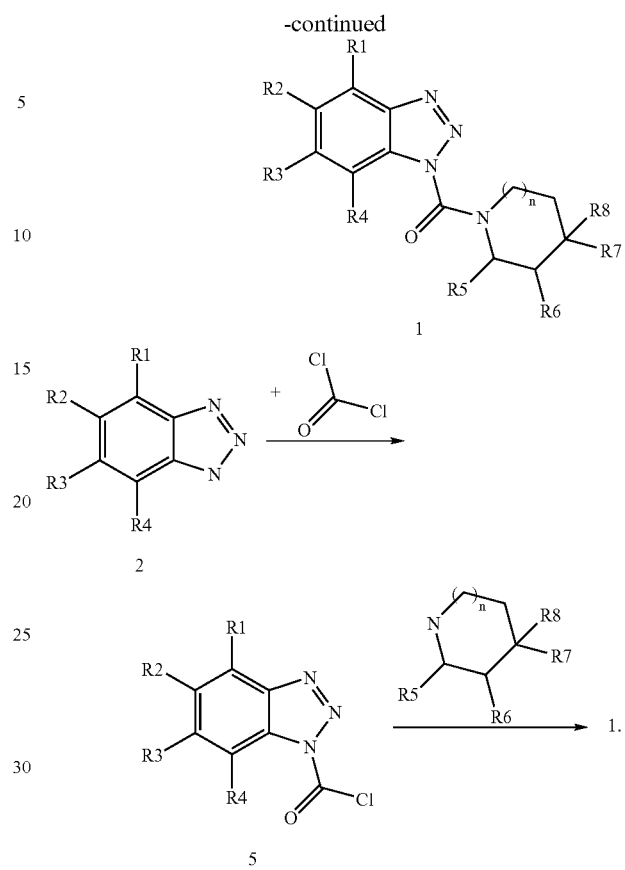

Since acids are usually liberated in these reactions, it is advisable to add bases such as pyridine, triethylamine, sodium hydroxide solution or alkali metal carbonates to increase the rate. The reactions can be carried out in wide temperature ranges. It has usually proved to be advantageous to operate at from about 0° C. to the boiling point of the solvent used. Examples of solvents employed are methylene chloride, THF, DMF, toluene, ethyl acetate, n-heptane, dioxane, and diethyl ether.

The compounds of the invention of formula I have a surprising inhibitory effect on hormone-sensitive lipase, HSL, an allosteric enzyme in adipocytes, which is inhibited by insulin and is responsible for the breakdown of fats in fat cells and thus for the transfer of constituents of fats into the bloodstream. Inhibition of this enzyme thus corresponds to an insulin-like effect of the compounds of the invention, which eventually leads to a reduction of free fatty acids in the blood and of blood glucose. They can thus be employed in treating metabolic derangements such as, for example, in non-insulin-dependent diabetes mellitus, in diabetic syndrome, in syndrome X and in direct pancreatic damage.

An inhibition of HSL in beta cells should lead to a direct recovery of insulin release (M. Winzell et al., Diabetes, Vol 52, August 2003, 2057–2065). The compounds of formula I according to the present invention can therefore also be used for insulin release.

The effect of the compounds of the invention of formula I was tested in the following enzyme assay system:

Substrate Preparation:

Preparation of NAG (NBD monoacyl glyceride) Substrate:
6 mg of phosphatidylcholine and 6 mg of phosphatidylinositol are each dissolved in 1 ml of chloroform. 10 mg of NAG are dissolved in 1 ml of chloroform. Two parts of phosphatidylinositol solution (i.e. 83.5 µl) and one part of phosphatidylcholine solution (i.e. 41.5 µl) and 100 µl of NAG solution are pipetted together into plastic scintillation vessels (final concentration in the assay: 0.0375 mg of phospholipid/ml; 0.05 mg NAG/ml). The chloroform (225 µl total volume) is completely removed by passing a stream of $N_2$ over the scintillation vessels. The dried substrate can be stored at 4° C. for up to 3 days. To prepare the phospholipid vesicles/micelles with intercalated NAG (on the day of the assay), the dried substrate is taken up in 20 ml of assay buffer (25 mM Tris/HCl, pH 7.4; 150 mM NaCl) and given two ultrasound treatments with an ultrasonic probe (Branson Sonifier Type II, standard microtip): 1st treatment setting 2, 2×1 min, followed by 1 min on ice each time; 2nd treatment setting 4, 2×min, followed by 1 min on ice each time. During this procedure, the color of the substrate solution changes from yellow (extinction maximum 481 nm) to red (extinction maximum 550 nm) owing to intercalation of NAG between the phospholipid molecules in the vesicles/micelles. Before use as substrate (within the next 2 h), the solution is incubated on ice for a further 15 min.

Indirect NAG Assay:

The assay is carried out in 1.5 ml Eppendorf vessels or 96-well plates at 30° C. for 60 min. To find HSL inhibitors, 10 µl of the test substance are introduced into assay buffer (25 mM Tris/HCl, pH 7.4; 150 mM NaCl) in the presence of 16.6% DMSO. 180 µl of the substrate solution (20 µg/ml phosphatidylcholine, 10 µg/ml phosphatidylinositol, 50 µg/ml NAG in assay buffer) are added. After preincubation at 30° C. for 15 min, 20 µl of the enzyme solution in assay buffer (diluted 1- to 4-fold) are pipetted in, and the extinction at 480 nm is immediately measured in a cuvette photometer (0.5 ml cuvette) or microtiter plate reader. After incubation at 30° C. for 60 min, the extinction is measured again. The increase in extinction at 480 nm is a measure of the enzymic activity. Under standard conditions, 20 µg of partially purified HSL lead to a change of 0.4=4000 arb. units in extinction.

Direct NAG Assay:

As an alternative to measurement of the change in extinction of the substrate solution, the products of the HSL reaction are investigated by phase separation/thin-layer chromatography. For this purpose, 1.3 ml of methanol/chloroform/heptane (10:9:7) and then 0.4 ml of 0.1 M NaOH are added to the incubation mixture (200 µl total volume, see indirect NAG assay) in 2 ml Eppendorf vessels. After vigorous mixing (10 sec), phase separation is initiated by centrifugation (800×g, 20 min, room temperature). Equivalent volumes (e.g. 0.4 ml) are taken from the aqueous upper phase, and the extinction at 481 nm is determined in a photometer. For thin-layer chromatography, the aqueous phase is dried (SpeedVac) and then taken up in 50 µl of tetrahydrofuran. 5 µl samples are loaded onto silica gel Si-60 plates (Merck). The chromatography is carried out with 78 ml of diethyl ether/22 ml of petroleum ether/1 ml of glacial acetic acid as the mobile phase. The amount of liberated fluorescent NBD-fatty acid is determined by Phosphorimaging (Molecular Dynamics, Storm 840 and ImageQuant Software) at an excitation wavelength of 460 nm and emission wavelength of 540–560 nm.

Enzyme Preparation:

Preparation of the Partially Purified HSL:

Isolated rat fat cells are obtained from epididymal adipose tissue from untreated male rats (Wistar, 220–250 g) by collagenase treatment in accordance with published methods (e.g. S. Nilsson et al., Anal. Biochem. 158, 1986, 399–407; G. Fredrikson et al., J. Biol. Chem. 256, 1981, 6311–6320; H. Tornquist et al., J. Biol. Chem. 251, 1976, 813–819). The fat cells from 10 rats are washed three times by flotation with 50 ml of homogenization buffer (25 ml Tris/HCl, pH 7.4, 0.25 M sucrose, 1 mM ETDA, 1 mM DTT, 10 µg/ml leupeptin, 10 µg/ml antipain, 20 µg/ml pepstatin) each time and finally taken up in 10 ml of homogenization buffer. The fat cells are homogenized in a Teflon-in-glass homogenizer (Braun-Melsungen) by 10 strokes at 1500 rpm and 15° C. The homogenate is centrifuged (Sorvall SM24 tubes, 5000 rpm, 10 min, 4° C.). The subnatant between the layer of fat at the top and the pellet is removed, and the centrifugation is repeated. The subnatant resulting therefrom is centrifuged again (Sorvall SM24 tubes, 20 000 rpm, 45 min, 4° C.). The subnatant is removed, and 1 g of heparin-Sepharose (Pharmacia-Biotech, CL-6B, washed 5× with 25 mM Tris/HCl, pH 7.4, 150 mM NaCl) is added. After incubation at 4° C. for 60 min (shaking at intervals of 15 min), the mixture is centrifuged (Sorvall SM 24 tubes, 3000 rpm, 10 min, 4° C.). The supernatant is adjusted to pH 5.2 by adding glacial acetic acid and is incubated at 4° C. for 30 min. The precipitates are collected by centrifugation (Sorvall SS34, 12 000 rpm, 10 min, 4° C.), and suspended in 2.5 ml of 20 mM Tris/HCl, pH 7.0, 1 mM EDTA, 65 mM NaCl, 13% sucrose, 1 mM DTT, 10 µg/ml leupeptin/pepstatin/antipain. The suspension is dialyzed against 25 mM Tris/HCl, pH 7.4, 50% glycerol, 1 mM DTT, 10 µg/ml leupeptin, pepstatin, antipain at 4° C. overnight and then loaded onto a hydroxiapatite column (0.1 g per 1 ml of suspension, equilibrated with 10 mM potassium phosphate, pH 7.0, 30% glycerol, 1 mM DTT). The column is washed with four volumes of equilibration buffer at a flow rate of 20 to 30 ml/h. The HSL is eluted with one volume of equilibration buffer containing 0.5 M potassium phosphate and then dialyzed (see above) and concentrated 5- to 10-fold by ultrafiltration (Amicon Diaflo PM 10 Filter) at 4° C. The partially purified HSL can be stored at—70° C. for 4 to 6 weeks.

Assay:

To prepare the substrate, 25–50 µCi of [3H]trioleoylglycerol (in toluene), 6.8 µmol of unlabeled trioleoylglycerol and 0.6 mg of phospholipids (phosphatidylcholine/phosphatidylinositol 3:1 w/v) are mixed, dried over $N_2$ and then taken up in 2 ml of 0.1 M KPi (pH 7.0) by ultrasound treatment (Branson 250, microtip, setting 1–2, 2×1 min with an interval of 1 min). After addition of 1 ml of KPi and renewed ultrasound treatment (4×30 sec on ice with intervals of 30 sec), 1 ml of 20% BSA (in KPi) is added (final concentration of trioleoylglycerol 1.7 mM). For the reaction, 100 µl of substrate solution are pipetted into 100 µl of HSL solution (HSL prepared as above, diluted in 20 mM KPi, pH 7.0, 1 mM EDTA, 1 mM DTT, 0.02% BSA, 20 µg/ml pepstatin, 10 µg/ml leupeptin) and incubated at 37° C. for 30 min. Addition of 3.25 ml of methanol/chloroform/heptane (10:9:7) and of 1.05 ml of 0.1 M $K_2CO_3$, 0.1 M boric acid (pH 10.5) is followed by thorough mixing and finally centrifugation (800×g, 20 min). After phase separation, one equivalent of the upper phase (1 ml) is removed, and the radioactivity is determined by liquid scintillation measurement.

Evaluation:

Substances are normally tested in four independent mixtures. The inhibition of the HSL enzymatic activity by a test substance is determined by comparing with an uninhibited control reaction. The $IC_{50}$ is calculated from an inhibition plot with min. 10 concentrations of the test substance. The GRAPHIT, Elsevier-BIOSOFT software package is used to analyze the data.

The compounds of Examples 1 to 55 showed inhibitions in the $IC_{50}$ range 0.04–5 μM in this assay.

The following example describe the invention in more detail without restricting it.

EXAMPLES

The example which follow were prepared according to one of the methods described below:

Method A:

To a solution of 2 mmol of 1H-benzotriazole in pyridine (5 ml) and dichloromethane (10 ml) is added a solution of the corresponding carbamoyl chloride (1 mmol) in dichloromethane (10 ml). The reaction mixture is stirred at RT (room temperature) for 16 h, then admixed with EtOAc (15 ml), and filtered through silica gel before the filtrate is concentrated. The product is purified by preparative HPLC and freeze dried.

Method B Examples:

a) Preparation of a benzotriazole-1-carbonyl chloride Solution

A solution of benzotriazole (6 g, 50.4 mmol) in THF (100 ml) is added dropwise to a phosgene solution (20% in toluene; 90 ml; 182 mmol) while cooling in ice. The ice bath is removed and the solution is then stirred at RT for a further 2 h. The solvent is distilled out and the residue is taken up in THF to give a total volume of 25 ml.

b) Reaction of the Benzotriazolecarbonyl Chlorides to Give the Corresponding Benzotriazole-1-carboxamides and Anilides In each case, 10 amines or anilines (2 mmol) are introduced into THF (1 ml), and pyridine (0.2 ml) is added. The mixtures are incubated with benzotriazole-1-carbonyl chloride solution (1 ml, ~2 mmol) and stirred at RT for 16 h. The mixtures are then diluted with ethyl acetate (5 ml) and filtered through silica gel, and the filtrate is evaporated to dryness in vacuo. The crude products are purified by flash chromatography.

Example 1

Methyl 3-(4-methylpiperidine-1-carbonyl)-3H-benzotriazole-5-carboxylate

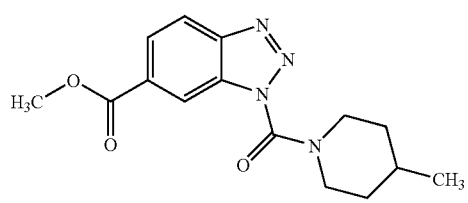

M+H+: 303.14

Example 2

(8-Aza-spiro[4,5]dec-8-yl)-benzotriazol-1-ylmethanone

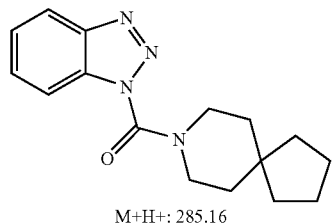

M+H+: 285.16

Example 3

Benzotriazol-1-yl-(6,7-dimethoxy-3,4-dihydro-1H-isoquinolin-2-yl)methanone

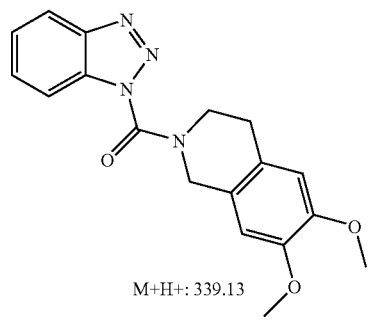

M+H+: 339.13

Example 4

(5-Phenoxybenzotriazol-1-yl)-(4-trifluoromethylpiperidin-1-yl)methanone

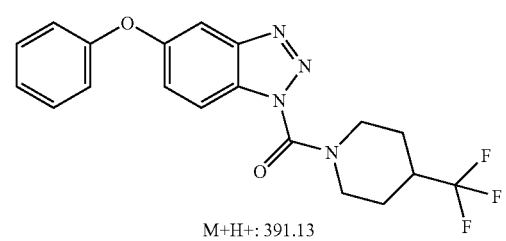

M+H+: 391.13

Example 5

(6-Chloro-5-fluorobenzotriazol-1-yl)-(4-methylpiperidin-1-yl)methanone

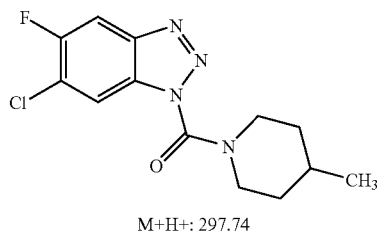

M+H+: 297.74

Example 6

Benzotriazol-1-yl-(4-bromopiperidin-1-yl)methanone

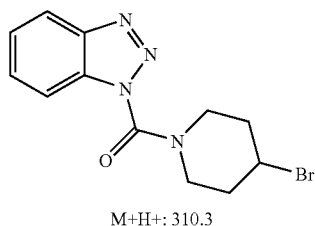

M+H+: 310.3

Example 7

Benzotriazol-1-yl-(4-trifluoromethylpiperidin-1-yl)methanone

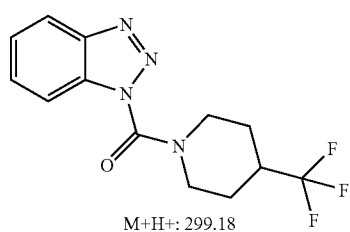

M+H+: 299.18

Example 8

Benzotriazol-1-yl-(1,3-dihydroisoindol-2-yl)methanone

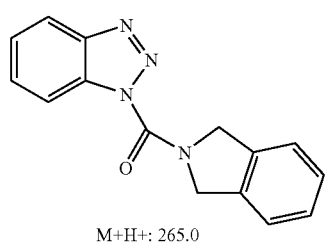

M+H+: 265.0

Example 9

Methyl-1-(3,6-dihydro-2H-pyridine-1-carbonyl)-1H-benzotriazole-5-carboxylate

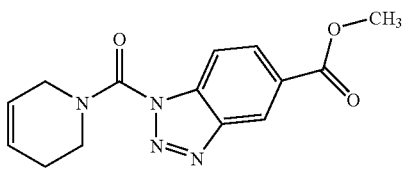

M+H+: 287.04

Example 10

(3,6-Dihydro-2H-pyridin-1-yl)-(5-nitrobenzotriazol-1-yl)methanone

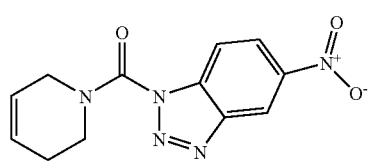

M+Na: 296.21

Example 11

(3,4-Dihydro-1H-isoquinolin-2-yl)-(5-nitrobenzotriazol-1-yl)methanone

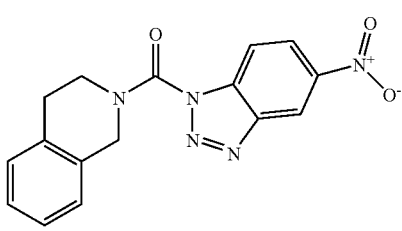

M+H+: 324.10

Example 12

(5-Bromobenzotriazol-1-yl)-(3,6-dihydro-2H-pyridin-1-yl)methanone

M+H+: 306.98

Example 13

(5-Bromobenzotriazol-1-yl)-(3-trifluoromethylpiperidin-1-yl)methanone

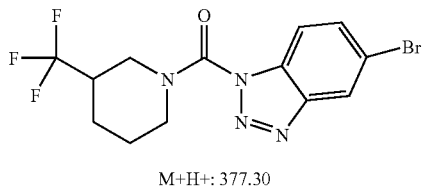

M+H+: 377.30

Example 14

(5-Bromobenzotriazol-1-yl)-(3,4-dihydro-1H-isoquinolin-2-yl)methanone

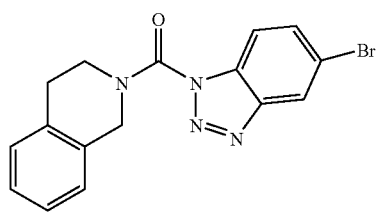

M+H+: 357.04

Example 15

Benzotriazol-1-yl-(octahydroisoindol-2-yl)methanone

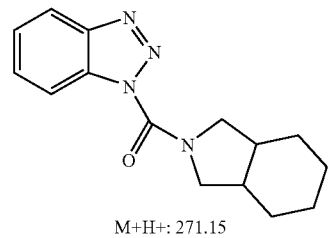

M+H+: 271.15

Example 16

(7-Amino-3,4-dihydro-1H-isoquinolin-2-yl)benzotriazol-1-ylmethanone

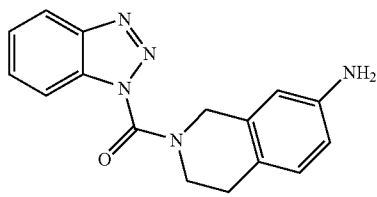

M+H+: 294.0

Example 17

(3,4-Dihydro-1H-isoquinolin-2-yl)-(5-methoxybenzotriazol-1-yl)methanone

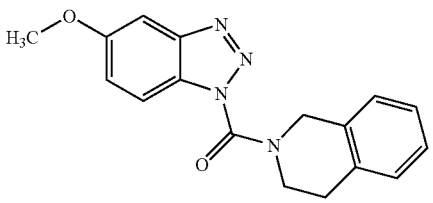

M+H+: 309.04

Example 18

(5-Methoxybenzotriazol-1-yl)-(3-methylpiperidin-1-yl)methanone

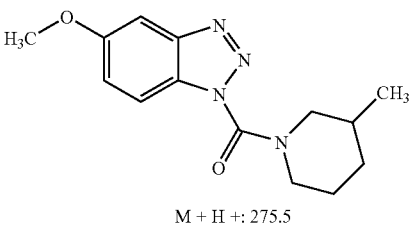

M + H +: 275.5

Example 19

(6-Aminobenzotriazol-1-yl)-(4-methylpiperidin-1-yl)methanone

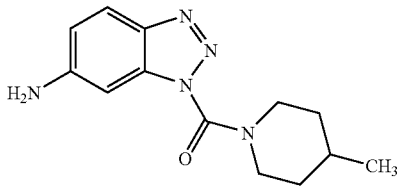

M + H +: 260.1

Example 20

(5-Chlorobenzotriazol-1-yl)-(4-methylpiperidin-1-yl)methanone

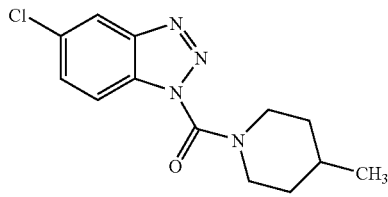

M + H +: 279.6

Example 21

Benzotriazol-1-yl-(1,2,6-triaza-spiro[2.5]oct-1-en-6-yl)methanone

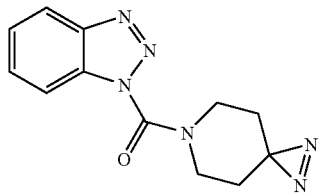

M + Na +: 279.19

Example 22

Benzotriazol-1-yl-(4-ethylpiperidin-1-yl)methanone

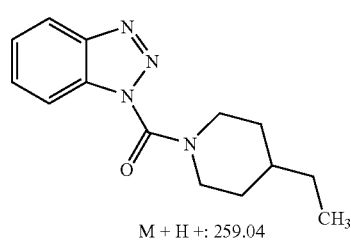

M + H +: 259.04

Example 23

(4-Methylpiperidin-1-yl)-(6-nitrobenzotriazol-1-yl)methanone

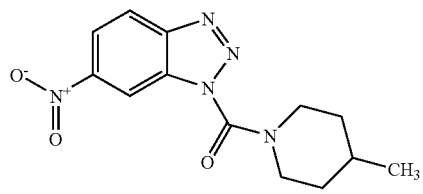

M + H +: 290.4

Example 24

Ethyl 1-(benzotriazole-1-carbonyl)piperidine-4-carboxylate

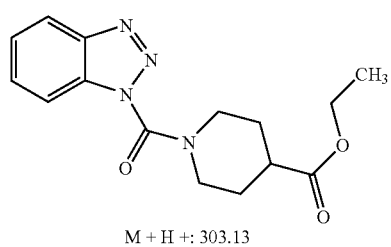

M + H +: 303.13

Example 25

Benzotriazol-1-yl-(4-methylpiperidin-1-yl)methanone

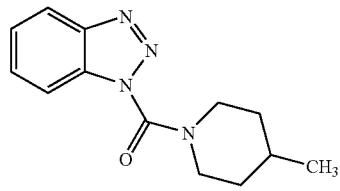

M + H +: 245.0

Example 26

3-(4-Methylpiperidine-1-carbonyl)-3H-benzotriazole-5-carbonitrile

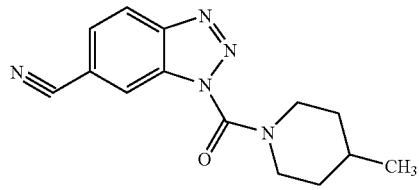

M + H +: 270.12

Example 27

Benzotriazol-1-yl-(3,4-dihydro-1H-isoquinolin-1-yl)methanone

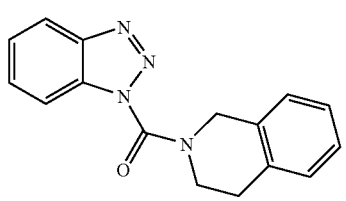

M + H +: 279.11

Example 28

Benzotriazol-1-yl-(3,4-dihydro-2H-quinolin-1-yl)methanone

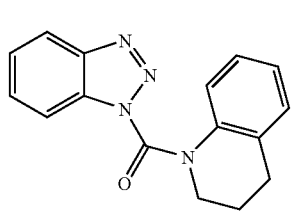

M + H +: 279.2

Example 29

(6-Methylbenzotriazol-1-yl)-pyrrolidin-1-ylmethanone

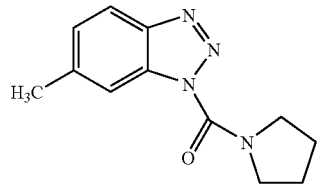

M + H +: 231.11

Example 30

Benzotriazol-1-yl-(3-methylpiperidin-1-yl)methanone

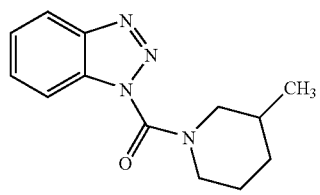

M + H +: 245.13

Example 31

Benzotriazol-1-yl-(3,4-dimethylpiperidin-1-yl)methanone

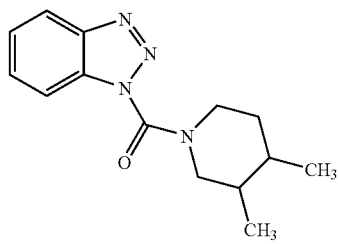

M + H +: 259.14

Example 32

[1-(4-Methylpiperidine-1-carbonyl)-1H-benzotriazol-5-yl]phenylmethanone

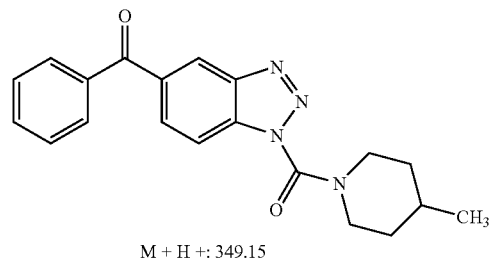

M + H +: 349.15

Example 33

(4-Methylpiperidin-1-yl)-(5-trifluoromethylbenzotriazol-1-yl)methanone

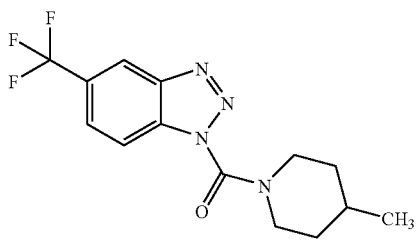

M + H +: 313.5

Example 34

(6-Bromobenzotriazol-1-yl)-(4-methylpiperidin-1-yl)methanone

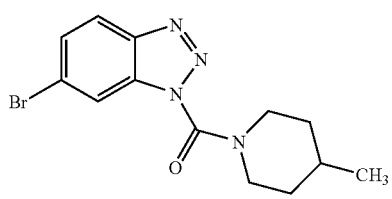

M + H +: 324.0

Example 35

Benzotriazol-1-yl-(4-tert-butylpiperidin-1-yl)methanone

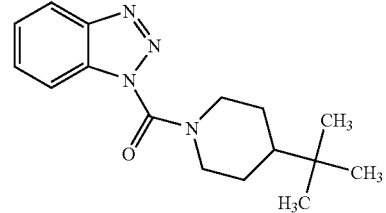

M + H +: 287.17

Example 36

[5-(Hydroxyphenylmethyl)benzotriazol-1-yl]-(4-methylpiperidin-1-yl)methanone

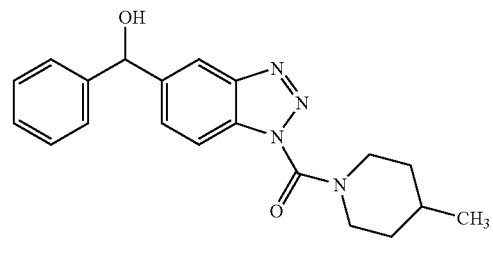

M + H +: 350.17

Example 37

(4-Methylpiperidin-1-yl)-(5-phenoxybenzotriazol-1-yl)methanone

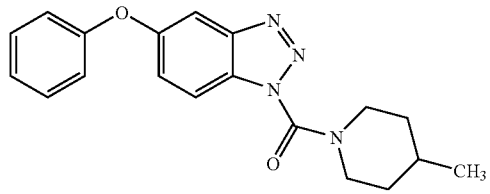

M + H +: 337.3

Example 38

(5-Cyclohexylsulfanylbenzotriazol-1-yl)-(4-methylpiperidin-1-yl)methanone

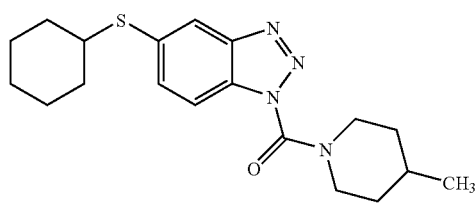

M+H+: 359.17

Example 39

Benzotriazol-1-yl-(4-isopropylpiperidin-1-yl)methanone

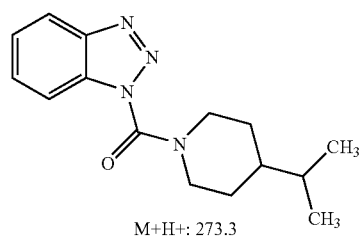

M+H+: 273.3

Example 40

(6-Chlorobenzotriazol-1-yl)-(4-methylpiperidin-1-yl)methanone

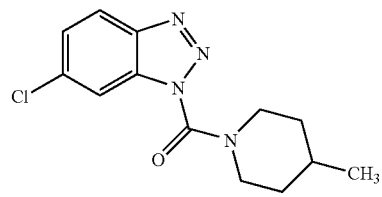

M+H+: 279.5

Example 41

Benzotriazol-1-yl-(6-methoxy-3,4-dihydro-1H-isoquinolin-2-yl)methanone

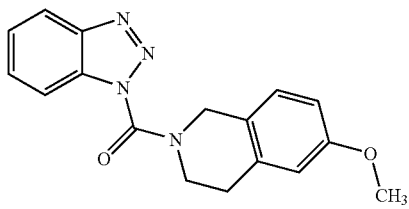

M+H+: 309.3

Example 42

Benzotriazol-1-yl-(4-benzylpiperidin-1-yl)methanone

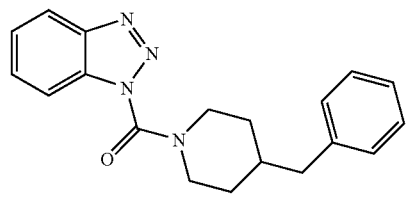

M+H+: 321.1

Example 43

(5-Bromobenzotriazol-1-yl)-(3-methylpiperidin-1-yl)methanone

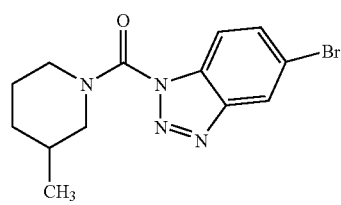

M+H+: 325.31

Example 44

1-(3,4-Dihydro-1H-isoquinoline-2-carbonyl)-1H-benzotriazole-5-carbonitrile

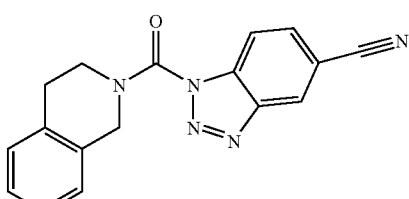

M+H+: 270.12

Example 45

(4-Chloro-6-trifluoromethylbenzotriazol-1-yl)-(3,4-dihydro-1H-isoquinolin-2-yl)methanone

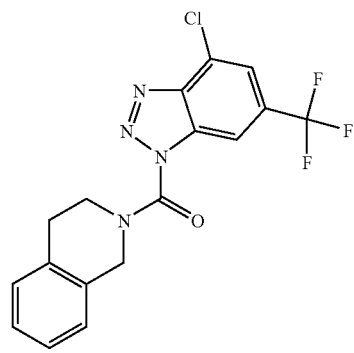

M+H+: 381.06

Example 46

1-(3,4-Dihydro-2H-quinolin-1-carbonyl)-1H-benzotriazole-5-carbonitrile

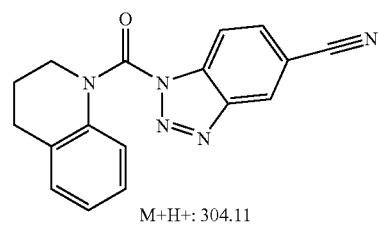

M+H+: 304.11

Example 47

(4-Chloro-6-trifluoromethylbenzotriazol-1-yl)-(3,6-dihydro-2H-pyridin-1-yl)methanone

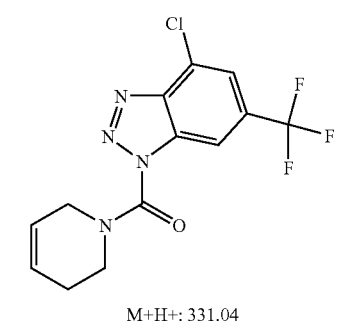

M+H+: 331.04

Example 48

Benzotriazol-1-yl-(7-methoxy-3,4-dihydro-1H-isoquinolin-2-yl)methanone

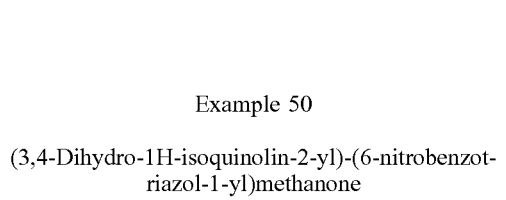

M+H+: 309.1

Example 49

(5-Methoxybenzotriazol-1-yl)-(4-methylpiperidin-1-yl)methanone

M+H+: 275.3

Example 50

(3,4-Dihydro-1H-isoquinolin-2-yl)-(6-nitrobenzotriazol-1-yl)methanone

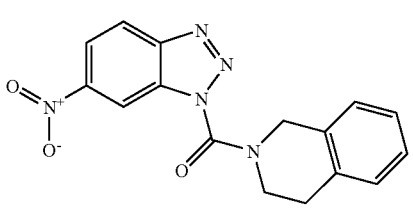

M+H+: 324.3

Example 51

(6-Benzoylbenzotriazol-1-yl)-(4-methylpiperidin-1-yl)methanone

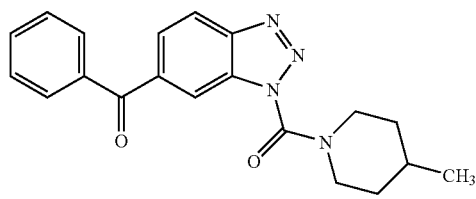

M+H+: 349.15

Example 52

Benzotriazol-1-yl-(7-nitro-3,4-dihydro-1H-isoquinolin-2-yl)methanone

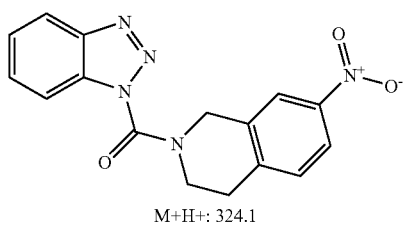

M+H+: 324.1

Example 53

Azepan-1-ylbenzotriazol-1-ylmethanone

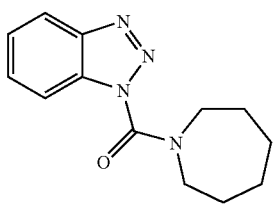

M+H+: 245.3

Example 54

Benzotriazol-1-yl-(4-chloropiperidin-1-yl)methanone

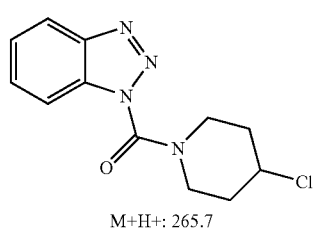

M+H+: 265.7

Example 55

Benzotriazol-1-yl-(3,6-dihydro-2H-pyridin-1-yl)methanone

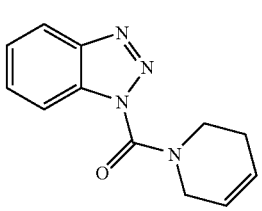

M+H+: 229.2.

The invention claimed is:

1. A benzotriazole of formula I,

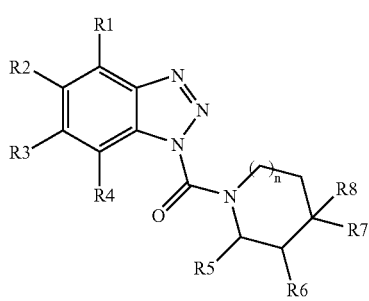

in which:

n is an integer selected from 0, 1 and 2

R1 to R8 are each H, except that one of R2 and R3 may be selected from

Br, Cl, $CH_3$, CN, NH2, $NO_2$, $CF_3$, $OCH_3$, phenoxy, benzoyl, CH(OH)-phenyl, S-cyclohexyl, and CO—$OCH_3$; or R1 is Cl and R3 is $CF_3$; or R2 is F and R3 is Cl; or one of R6 and R7 may be selected as follows:

R6 is $CH_3$ or R7 is selected from $CH_3$, $C_2H_5$, $CH(CH_3)_2$, $C(CH_3)_3$, $CF_3$, Br, Cl, benzyl and CO—$OC_2H_5$; or R6 and R7 each are $CH_3$; or R6 and R7 may be replaced by a double bond between the ring carbon to which they are attached; or R5 and R6 or R6 and R7 may, in combination with the carbon to which they are attached, form a benzo-fused ring or, when n is 0, may form cyclohexanediyl, the ring formed from R6, R7 and the carbons to which they are attached being optionally substituted singly by $NH_2$ or $NO_2$ or substituted singly or doubly by $OCH_3$; and R7 and R8, together with the carbon to which they are attached, may form cyclopentyl, diazirinediazirine or =$CH_2$; provided, however, that when R1 to R5 and R8 are H, and R6, R7 and the carbons to which they are attached form a benzo-fused ring, n is not 1, and when R1 and R3–R8 are H and R2 is $CH_3$, n is not 1 and when R1 to R8 are each H, n is 2.

2. A benzotriazole of formula I as claimed in claim 1,

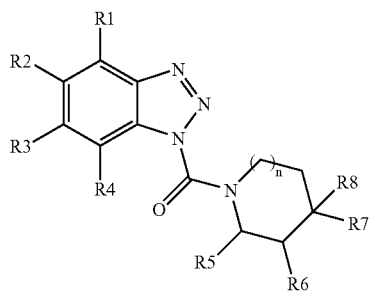

in which:
R1 to R8 are each H, except that one of R2 and R3 may instead be selected from the following substituents:
R2 is selected from Br, Cl, CN, $NO_2$, $CF_3$, $OCH_3$, phenoxy, benzoyl, CH(OH)-phenyl, S-cyclohexyl, and CO—$OCH_3$; or
R3 is selected from $CH_3$, CN, Br, Cl, $NH_2$, $NO_2$, and benzoyl.

3. A benzotriazole of formula I as claimed in claim 1, in which:
R1 to R8 are each H; except that one of R2 and R3 may instead be selected from the following substituents:
R2 is selected from Br, Cl, $NO_2$, $OCH_3$, phenoxy, and CO—$OCH_3$; or
R3 is $NH_2$; or
R2 is F and R3 is Cl; or
n is 1 or 2 and
one of R6 and R7 is selected from the following substituents:
R6 is $CH_3$; or R7 is selected from $CH_3$, $CF_3$ and Br; or
R6 and R7 may be replaced by a double bond between the ring carbons to which they are attached; or
R6 and R7 may, in combination with the carbons to which they are attached, form a benzo-fused ring, which may be optionally substituted singly by $NH_2$ or substituted singly or doubly by $OCH_3$; and
R7 and R8 together, with the carbon to which they are attached, form a cyclopentyl; or
n is 0 and
R6 and R7, together with the carbons to which they are attached, form a benzo-fused ring or cyclohexanediyl.

4. A benzotriazole of formula I as claimed in claim 1, wherein
R1 to R8 are each H; except that one of R2 and R3 may instead be selected from the following substituents:
R2 is selected from Br, CN, $CF_3$, $OCH_3$, phenoxy, benzoyl, CH(OH)-phenyl, and S-cyclohexyl; or
R3 is selected from CN, Br, Cl, $NO_2$, and benzoyl; or R1 is Cl and R3 is $CF_3$; or
n is 1 and
one of R6 and R7 is selected from the following substituents:
R6 is $CH_3$; or
R7 is selected from $CH_3$, $C_2H_5$; $CH(CH_3)_2$, $C(CH_3)_3$, benzyl and CO—$OC_2H_5$; or
R6 and R7 are each $CH_3$; or R6 and R7 may be replaced by a double bond between the ring carbons to which they are attached; or
R5 and R6 or R6 and R7 may, in combination with the carbons to which they are attached, form a benzo-fused ring;

provided, however, that when R1 to R5 and R8 are H and R6, R7 and the carbon to which they are attached form a benzo-fused ring, n is not 1.

5. A benzotriazole selected from the group consisting of the compounds having the following structures:

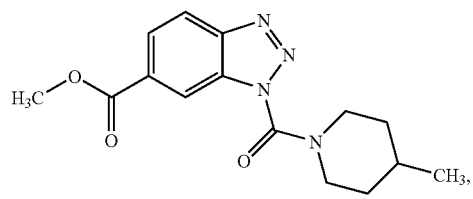

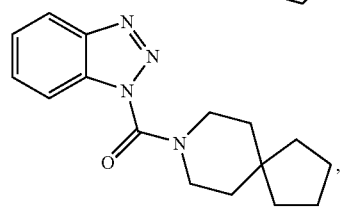

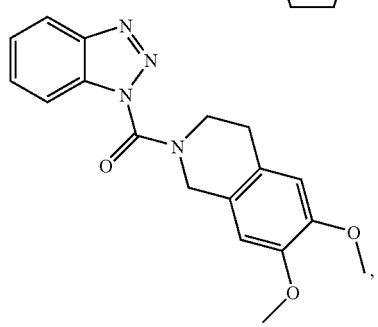

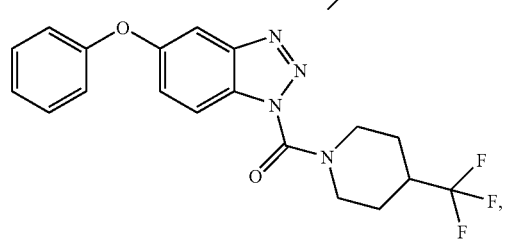

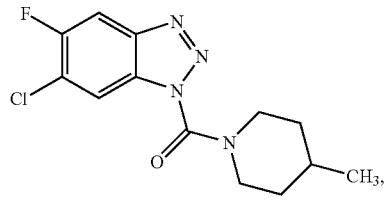

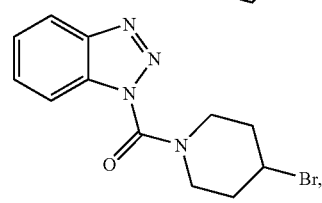

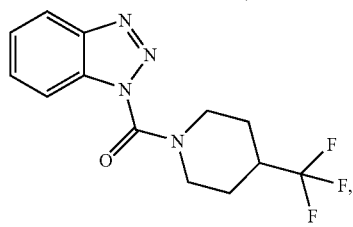

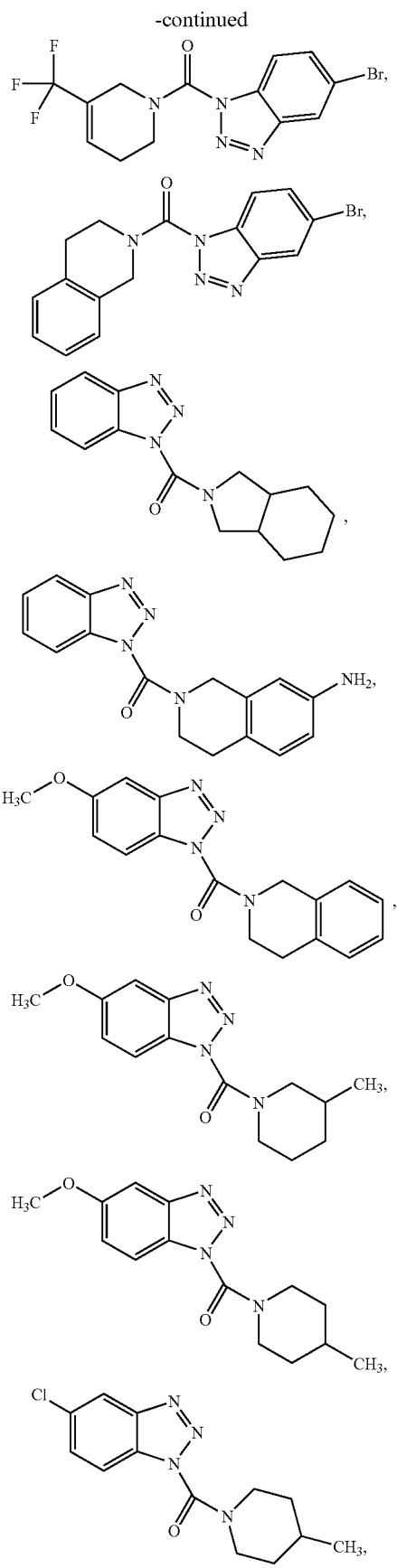
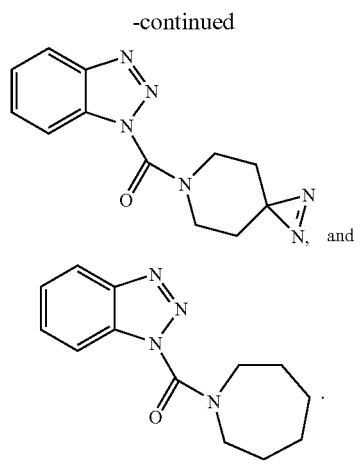
6. A benzotriazole selected from the group consisting of the compounds having the following structures:
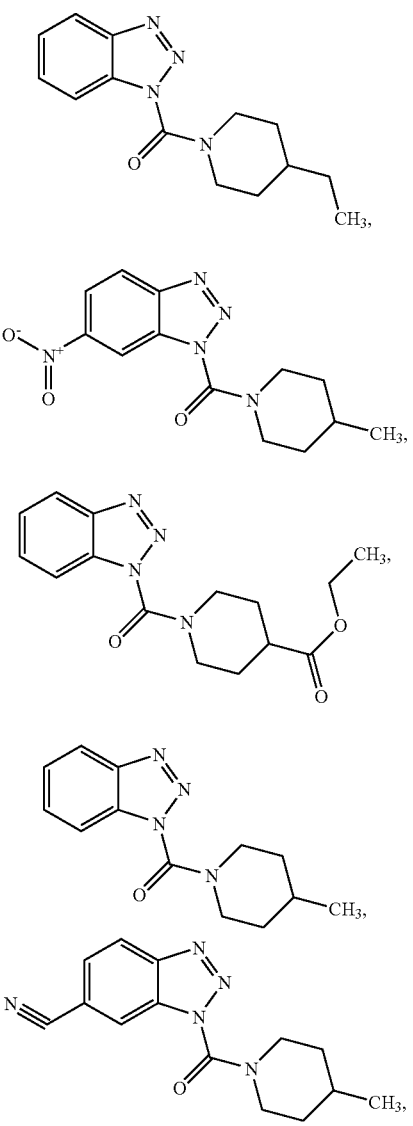

-continued
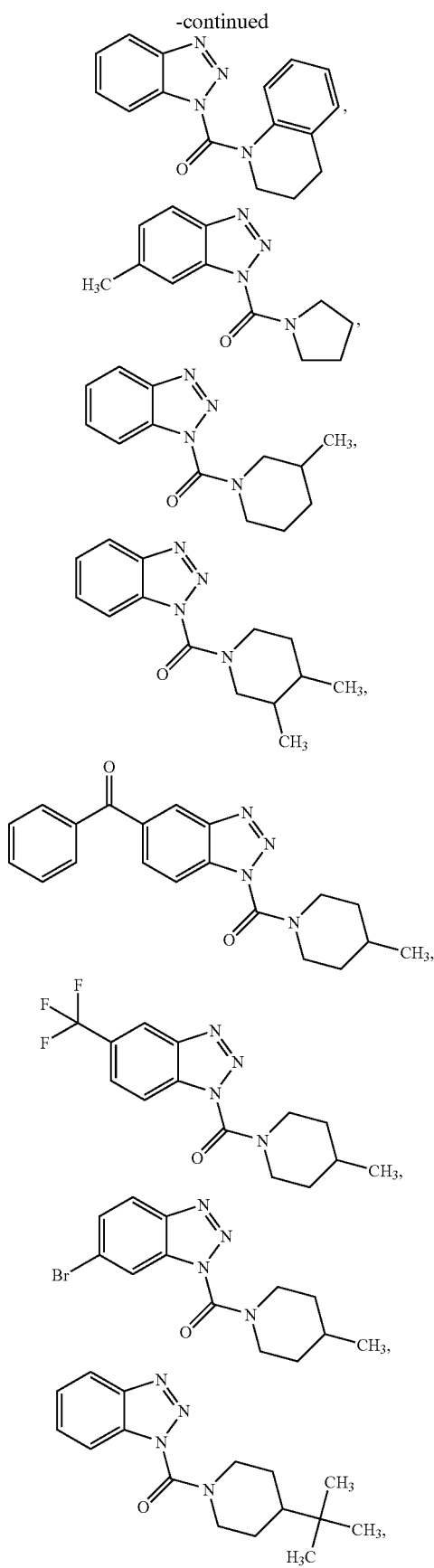
-continued
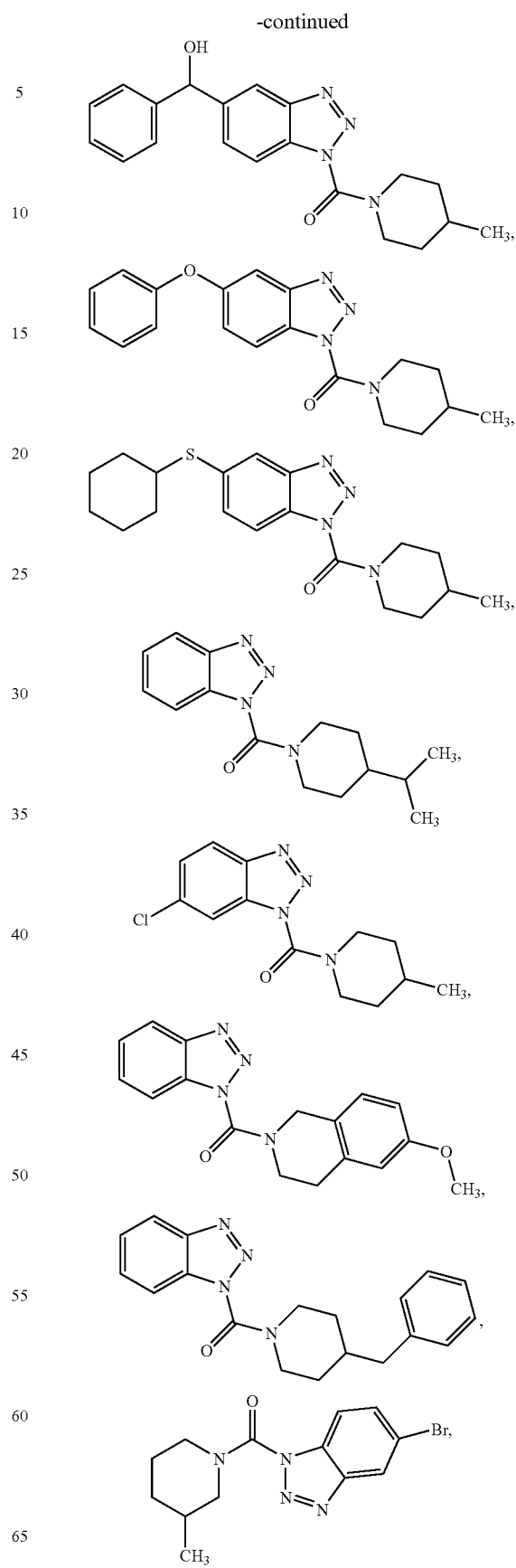

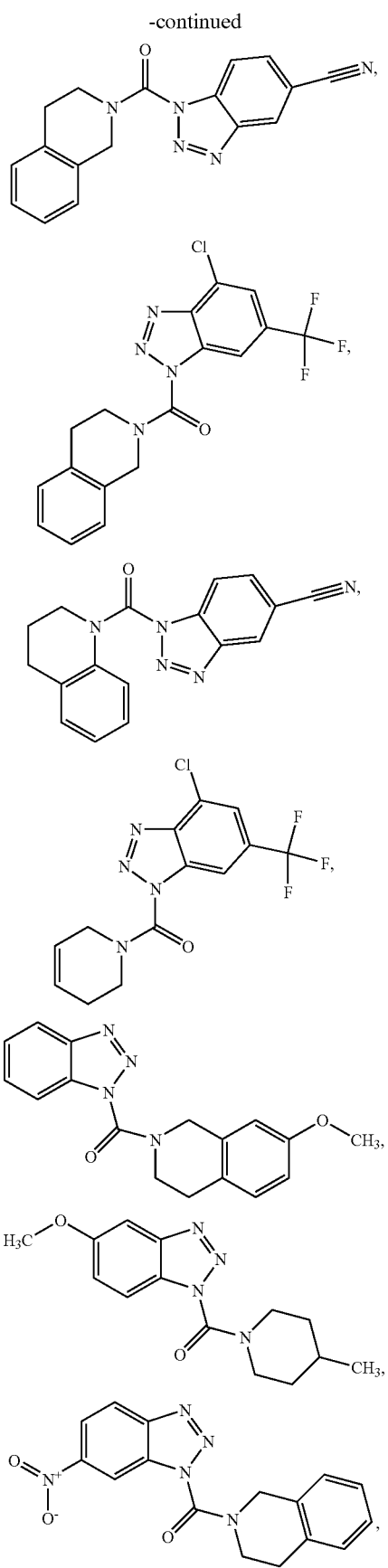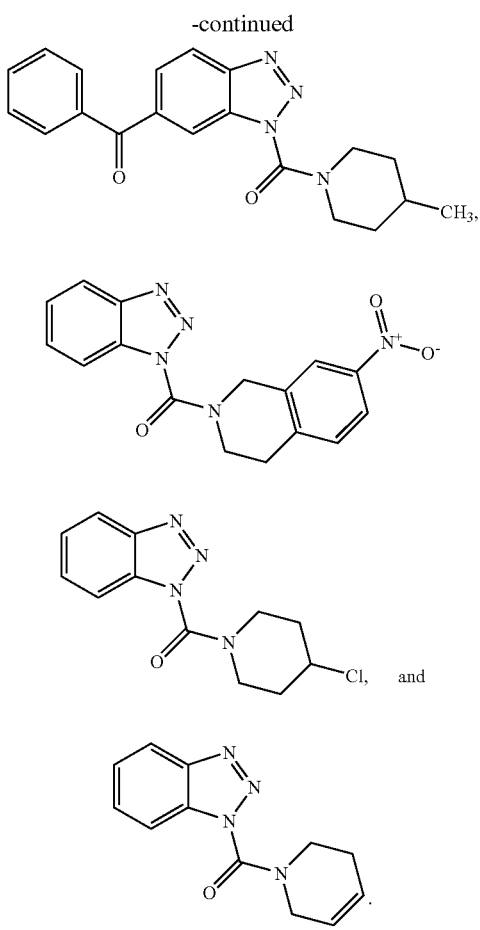
7. A benzotriazole as claimed in claim 6 selected from the group consisting of the compounds having the following structures:
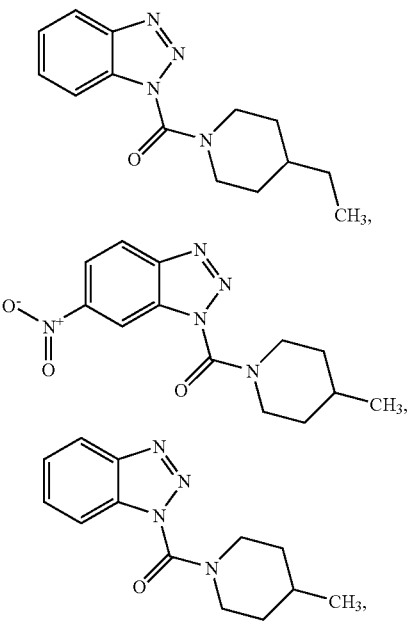

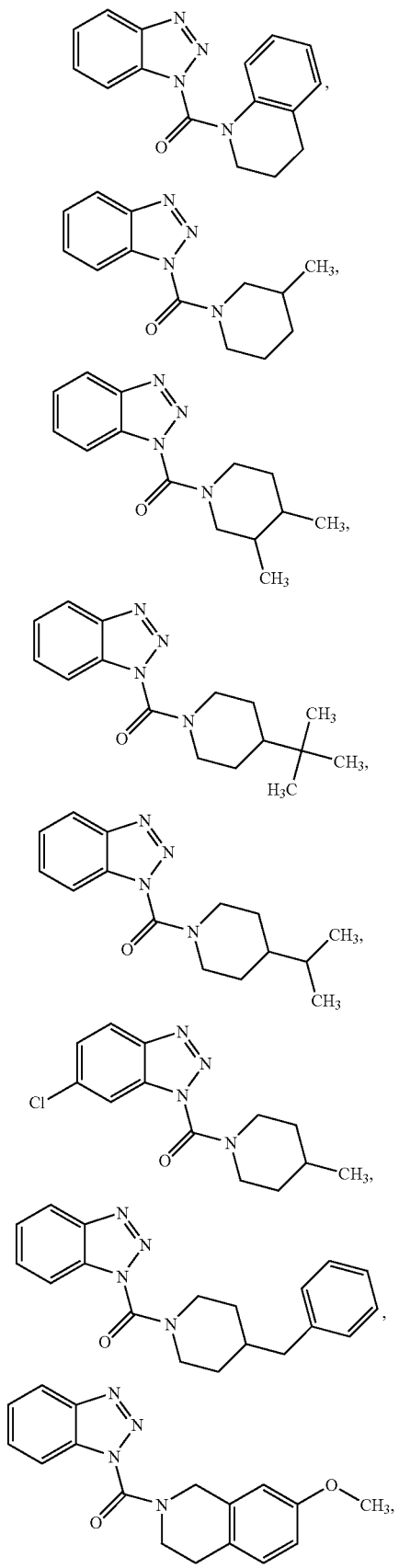
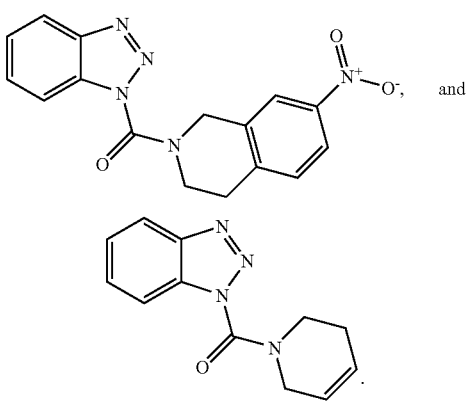
8. A benzotriazole as claimed in claim 7 selected from the group consisting of the compounds having the following structures:
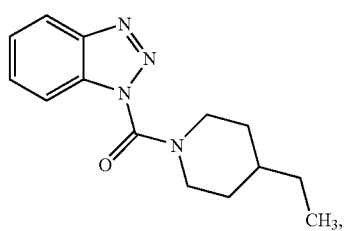
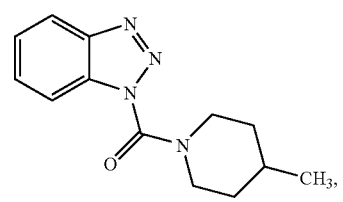
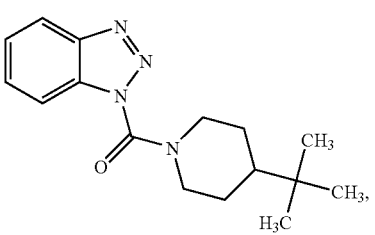
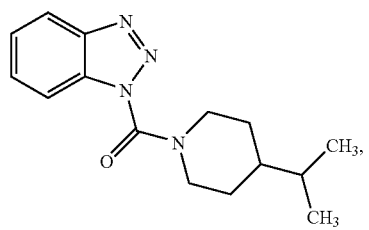
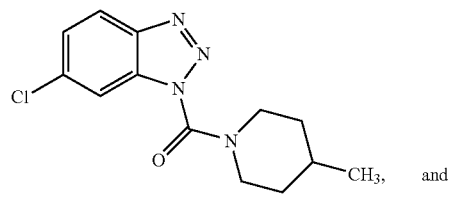

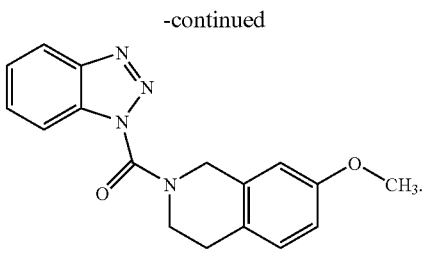

9. A process for preparing the compounds of formula I as claimed in claim 1, which comprises
   a) acylating benzotriazole 2 with carbamoyl chlorides 3, or
   b) initially reacting benzotriazoles 2 with phosgene and then reacting the resulting benzotriazolecarbonyl chlorides 5 with amines or anilines to give the compounds of the formula I, in which the substituents are as defined in claim 1:

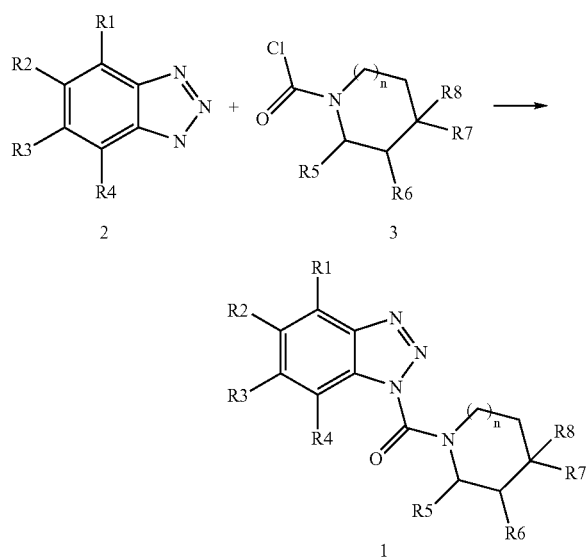

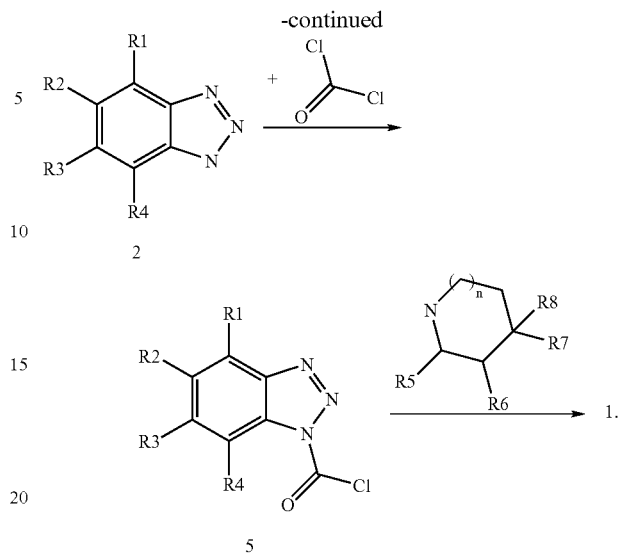

10. A pharmaceutical composition comprising, as an active ingredient, a benzotriazole of formula I as claimed in claim 1.

11. A method of inhibiting hormone-sensitive lipase, HSL, for treating a disease selected from the group consisting of non-insulin-dependent diabetes mellitus, diabetes syndrome, or syndrome X comprising administering to a patient in need thereof an effective amount of a pharmaceutical composition as claimed in claim 10.

12. A method of treatment of non-insulin-dependent diabetes mellitus or of diabetic syndrome or syndrome X, comprising administering to a patient in need thereof an effective amount of a pharmaceutical composition as claimed in claim 10.

13. A method for the treatment of non-insulin-dependent diabetes mellitus or of diabetic syndrome X, comprising administering to a patient in need thereof an effective amount of at least one benzotriazole of formula I as claimed in claim 1.

* * * * *